(12) United States Patent
Kunde et al.

(10) Patent No.: US 6,376,656 B1
(45) Date of Patent: *Apr. 23, 2002

(54) REACTIVE DYESTUFFS CONTAINING MONOHAGENOTRIAZINE AND VINYLSULFONE GROUPS, THEIR PREPARATION AND USE

(75) Inventors: Klaus Kunde, Neunkirchen-Seelscheid; Karl-Josef Herd, Odenthal, both of (DE)

(73) Assignee: DyStar Textilfarben GmbH & Co. Deutschland KG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/426,590

(22) Filed: Oct. 26, 1999

Related U.S. Application Data

(62) Division of application No. 09/031,805, filed on Feb. 27, 1998, now Pat. No. 6,025,478, which is a continuation of application No. 08/698,299, filed on Aug. 15, 1996, now abandoned, which is a continuation of application No. 08/333,164, filed on Nov. 1, 1994, now abandoned.

(30) Foreign Application Priority Data

Nov. 8, 1993 (DE) ............................................ 43 38 117

(51) Int. Cl.[7] ...................... C09B 62/04; C09B 62/503; D06P 3/10; D06P 3/66
(52) U.S. Cl. ...................... 534/637; 534/617; 534/642
(58) Field of Search .................. 534/617, 632, 534/633, 634, 635, 636, 637, 642; 540/126; 544/626

(56) References Cited

U.S. PATENT DOCUMENTS

| 4,912,244 A | 3/1990 | Tzikas et al. ................. 558/23 |
| 5,274,083 A | 12/1993 | Herd et al. ................. 534/618 |
| 6,025,478 A | 2/2000 | Kunde et al. ............... 534/618 |

FOREIGN PATENT DOCUMENTS

| EP | 0 070 806 | 1/1983 |
| EP | 0 070 807 | 1/1983 |
| EP | 0 074 928 | 3/1983 |
| GB | 1 576 237 | 10/1980 |
| WO | WO 90/09983 | 9/1990 |
| WO | WO 91/13866 | 9/1991 |

OTHER PUBLICATIONS

Derwent Abstract, Week K21, p. 9, Textiles: Paper: Cellulose; CIBA F06, 30180 K/13=158065–759; "Reactive dye contg.sulphato:ethyl–sulphonyl gps . . . " Ciba–Geigy AG, Sep. 16, 1981.

*Primary Examiner*—Floyd D. Higel
(74) *Attorney, Agent, or Firm*—Connolly Bove Lodge & Hutz LLP

(57) ABSTRACT

Reactive dyestuffs of the formula (I)

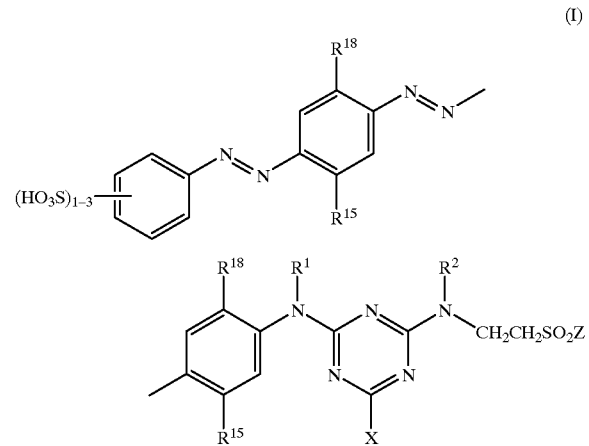

wherein
- $R^1$ denotes H or unsubstituted or substituted $C_1$–$C_4$-alkyl,
- $R^2$ denotes $C_1$–$C_4$-alkyl,
- X denotes F, Cl or Br,
- Z denotes —CH=CH$_2$ or —CH$_2$CH$_2$—OSO$_3$H,
- $R^{15}$ denotes H, $C_1$–$C_4$-alkyl, $C_1$–$C_4$-alkoxy, Cl, Br, acylamino, amino carbonylamino, $C_1$–$C_4$-alkylsulphonylamino or arylsulphonylamino and
- $R^{18}$ denotes H, $C_1$–$C_4$-alkyl, $C_1$–$C_4$-alkoxy, OH or SO$_3$H.

The invention also relates to a process for the preparation of the reactive dyestuff and their use of dyeing fibre materials containing OH groups and NH groups.

5 Claims, No Drawings

REACTIVE DYESTUFFS CONTAINING MONOHAGENOTRIAZINE AND VINYLSULFONE GROUPS, THEIR PREPARATION AND USE

This application is a divisional of application Ser. No. 09/031,805 filed Feb. 27, 1998, now U.S. Pat. No. 6,025,478 which is a continuation of application Ser. No. 08/698,299 filed Aug. 15, 1996 now abandoned, which is a continuation of application Ser. No. 08/333,164 filed on Nov. 1, 1994 now abandoned.

The invention relates to new bi- and polyfunctional reactive dyestuffs, their preparation and their use.

Although bifunctional reactive dyestuffs are known, for example, from DE-A-2 614 550, EP-A-70 807, EP-A-70 806 and EP-A-74 928 and tri- and tetrafunctional reactive dyestuffs are known, for example, from EP-A-395 951, the known reactive dyestuffs still have diverse disadvantages in terms of their use, for example too low a fixing yield.

The present invention relates to new reactive dyestuffs of the formula

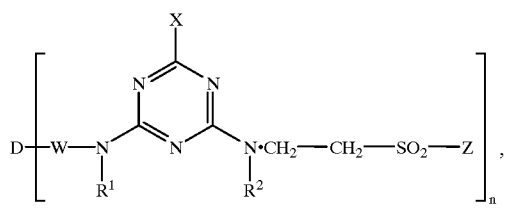

(I)

wherein

D is the radical of an organic dyestuff from the monoazo, polyazo, metal complex azo, anthraquinone, phthalocyanine, formazan, azomethine, dioxazine, phenazine, stilbene, triphenylmethane, xanthene, thioxanthone or the nitroaryl series, W denotes a direct bond or bridge member, in particular represents a direct bond, $R^1$ denotes H or $C_1$–$C_4$-alkyl, which can be substituted, for example, by OR, $OSO_3H$, $SO_3H$, COOH or halogen, R represents H, $CH_3$ or $C_2H_5$, $R^2$ denotes $C_1$–$C_4$-alkyl, in particular methyl, Z represents —$CH_2$—$CH_2$—$OSO_3H$ or —CH=$CH_2$, X represents F, Cl or Br and n denotes 1 or 2.

The following statements apply to the alkyl, aryl, aralkyl, hetaryl, alkoxy, halogen and acylamino radicals mentioned in the present Application and to the bridge members:

Alkyl groups are understood as meaning, in particular, those having 1 to 4 C atoms, which can optionally contain substituents, for example halogen, such as Cl or Br, OH, CN, $CO_2H$, $SO_3H$ or $OSO_3H$.

Alkoxy radicals are understood as meaning, in particular, those having 1 to 4 C atoms.

Halogen is understood as meaning, in particular, chlorine or fluorine.

Acylamino radicals are understood as meaning, in particular, those having 1 to 4 C atoms, such as formylamino, acetylamino, propionylamino and n-butyrylamino.

Suitable bridge members W are, for example:

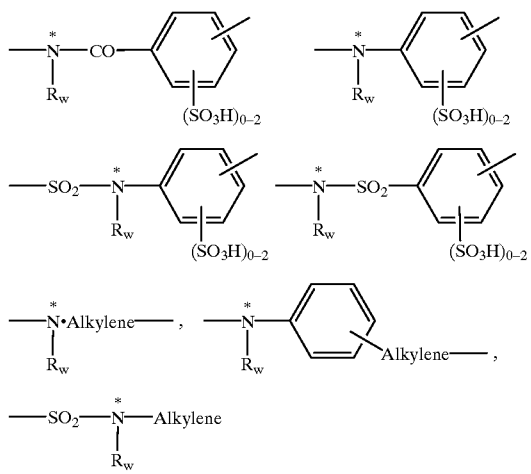

wherein $R_w$ represents hydrogen or alkyl, and Alkylene denotes an alkylene radical having 1 to 6 C atoms, where * identifies the atom or group bonded to the chromophore D.

Alkylene radicals which may be mentioned are:

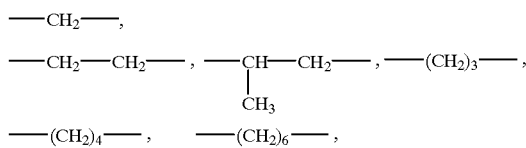

The invention furthermore relates to the preparation of the reactive dyestuffs of the formula (I):

a) either by condensation of dyestuffs of the formula

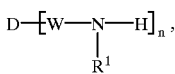

(II)

wherein

D, W, $R^1$ and n have the abovementioned meaning, with n moles of trihalogenotriazines of the formula (III)

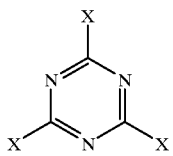

to give compounds of the formula

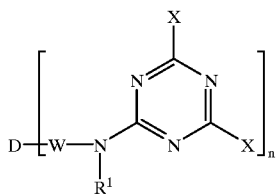
(IV)

and further condensation of the compounds of the formula (IV) with n moles of the components of the formula

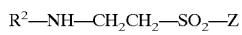
(V), wherein

R² and Z have the abovementioned meaning, or b) in the reverse sequence, by condensation of trihalogenotriazines of the formula (III) with the components of the formula (V) to give the primary condensation products

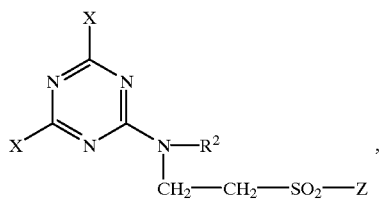
(VI)

wherein

R² and Z have the abovementioned meaning, and further condensation of n moles of the compounds of the formula (VI) with the dyestuffs of the formula (II) or c) by condensation of suitable precursors with the trihalogenotriazines (III) and the components of the formula (V) or by condensation of suitable precursors with the primary condensation products of the formula (VI) and subsequent dyestuff synthesis.

The invention furthermore relates to a process for the preparation of compounds of the formula (V), characterized in that compounds of the formula

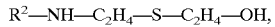

which are obtained by reaction of 3-alkyl-2-oxo-oxazolidinones of the general formula

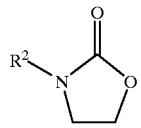

with 2-mercaptoethanol, are converted by oxidation, in particular with $H_2O_2$, into compounds of the formula

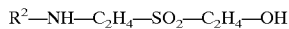

and these are then converted into compounds of the general formula (V) in the customary manner.

The condensations of the starting components with the trihalogenotriazines are carried out in aqueous or organic-aqueous media in the presence of acid-binding agents, regardless of the sequence. Depending on the nature of the starting components, the first stage of the condensation is carried out here in pH ranges of 2 to 8, preferably 3 to 7, and at temperatures of 0 to 40° C., preferably 0 to 25° C. Replacement of the second halogen atom of the triazine takes place in the pH range from 4 to 10, preferably 5 to 9, and in the temperature range from 0 to 60° C., preferably 0 to 30° C.

Acid-binding agents are, for example, carbonates, hydroxides or phosphates, such as sodium carbonate, sodium bicarbonate, dilute sodium hydroxide solution, di- or trisodium phosphate or sodium fluoride.

If the condensation or the dyestuff synthesis is to lead directly to a dyestuff solution or to a liquid dyestuff preparation, it may be advantageous to use lithium carbonates or lithium hydroxide, if appropriate together with solubilizing agents and/or stabilizing buffer systems. Other conversion reactions of the dyestuffs or precursors thereof, such as metallization reactions, sulphonations or introduction of acylamino groupings, can in general be carried out at any desired stages of the dyestuff syntheses.

Particularly useful dyestuffs from the anthraquinone, phthalocyanine, formazan, azomethine, dioxazine, phenazine, stilbene, triphenylmethane, xanthene, thioxanthone or nitroaryl series are water-soluble formazan, anthraquinone and phthalocyanine dyestuffs, and in particular those which contain sulphonic acid and/or carboxylic acid groups. The dyestuffs can be either metal-free or metal-containing, the copper, nickel, chromium and cobalt complexes being of preferred interest under the metal complexes.

Suitable dyestuff radicals D of this class or the dyestuffs containing amino groups on which the dyestuffs of the formula (I) are based are described in a very large number in the literature. Examples which may be mentioned here are:

EP-A 54 515, EP-A 69 703, EP-A 70 807, DE-3 222 726, DE-A 2 650 555, DE-A 3 023 855, DE-A 2 847 938, DE-A 2 817 780, GB-A 2 057 479, DE-A 2 916 715, DE-A 2 814 206, DE-A 3 019 936, EP-A 45 488 and Venkataraman: The Chemistry of Synthetic Dyes, Volume VI, Chapter II, pages 211–325, New York, London; 1972.

A radical which contains one or more groups which confer water-solubility, in particular sulpho groups, but no further fibre-reactive radicals being a particularly suitable radical of an organic dyestuff of this class.

Preferred dyestuffs are those of the following formula (1) to (8), wherein, in general, B' comprises a radical of the formula

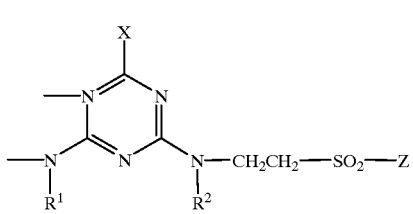
(VIb)

and $R^1$, X, $R^2$ and Z have the abovementioned meaning

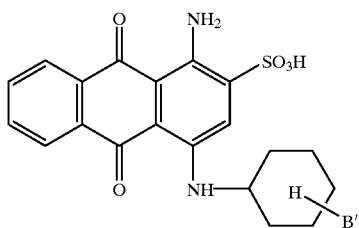
(1)

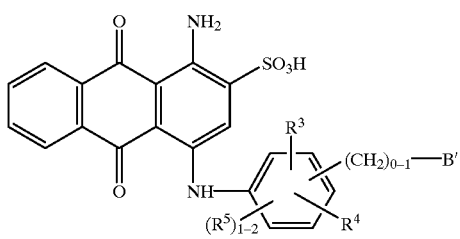
(2)

wherein
$R^3$=H, methyl, methoxy or chlorine
$R^4$=H or $SO_3H$ and
$R^5$=H, methyl or ethyl

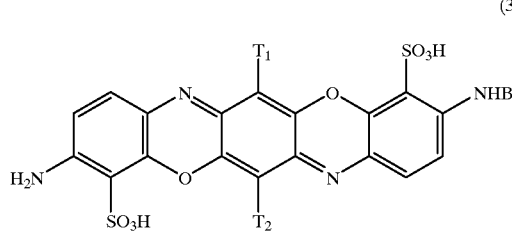
(3a)

wherein
B denotes a radical of the formula

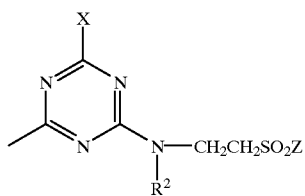
(VIa)

in which the substituents X, $R^2$ and Z have the abovementioned meaning, and

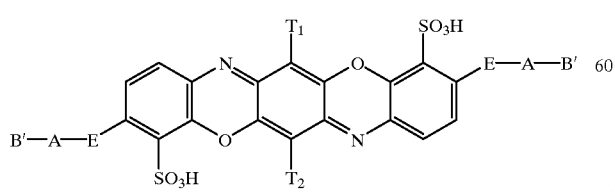
(3b)

wherein

A represents an optionally substituted phenylene or an optionally substituted aromatic-aliphatic bridge member, or represents a straight-chain or branched $C_1$–$C_6$-alkylene which is optionally interrupted by groupings containing heteroatoms, such as $NR^6$, O or S, and can be substituted by $C_1$–$C_6$-alkoxy, $OSO_3H$, $SO_3H$, COOR or halogen, and wherein, within a bridge member A, the group $NR^6$ can also form a heterocyclic aliphatic ring with the group $NR^1$, in particular

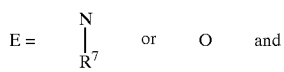

$T_1$ and $T_2$=independently of one another H, Cl, Br, $C_1$–$C_2$-alkyl, $OCH_3$, $OC_2H_5$, acylamino, $C_1$–$C_2$-alkoxycarbonyl, $R_6$ and $R_7$=independently of one another H or $C_1$–$C_4$-alkyl, which can be substituted by OR, $OSO_3H$, $SO_3H$, COOR or halogen, R=H, $CH_3$ or $C_2H_5$.

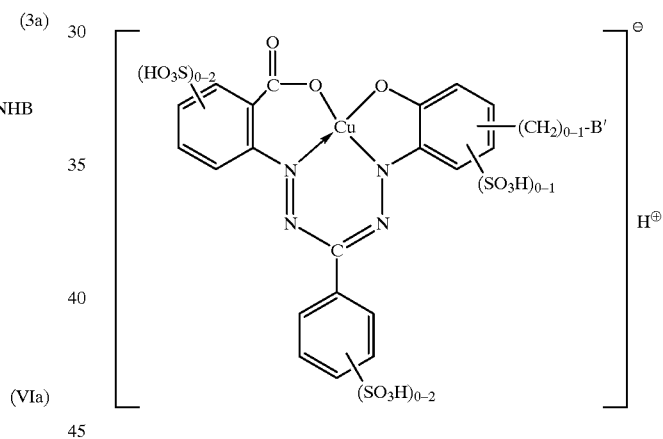
(4)

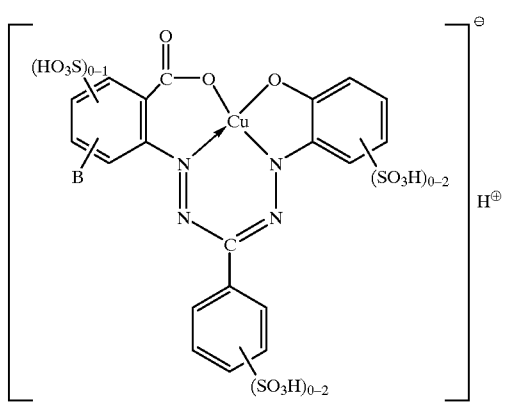
(5)

-continued (6)

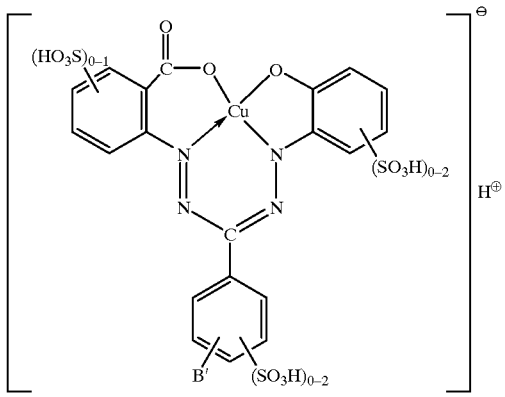

(7)

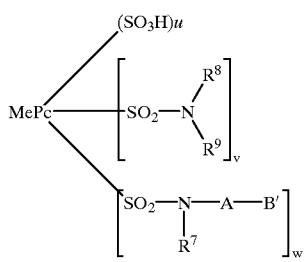

wherein
Me=Cu or Ni,
Pc=the radical of a phthalocyanine,
u+v+w=3.4–4.0, with the proviso that
u=0.8–2.0,
v=0–1.0 and
w=1.0–3.0, and
A has the abovementioned meaning,
$R^7$ has the abovementioned meaning,
$R^8$ and $R^9$=H or $C_1$–$C_2$-alkyl, which is optionally substituted by OH, $OSO_3H$, $SO_3H$ or COOH.

(8)

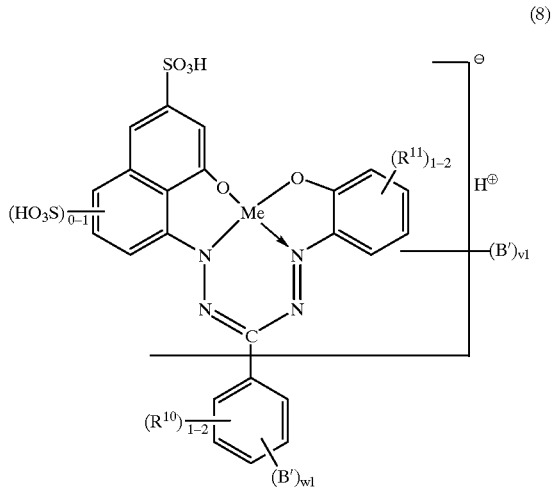

wherein
v1 and w1=0 or 1, where w1 is not identical to v1,
$R^{10}$ and $R^{11}$ independently of one another are H, $C_1$–$C_4$-alkyl, $C_1$–$C_4$-alkoxy, OH, halogen, COOH, $NO_2$, $SO_3H$, sulphonamido, $C_1$–$C_4$-alkylcarbonylamino, optionally substituted phenylcarbonylamino, $C_1$–$C_4$-alkylsulphonylamino or optionally substituted phenylsulphonylamino.

Other particularly useful dyestuffs of this series are water-soluble azo dyestuffs, and in particular those which contain sulphonic acid and/or carboxylic acid groups. The dyestuffs can be either metal-free or metal-containing, the copper, nickel, chromium and cobalt complexes being of preferred interest among the metal complexes.

Suitable dyestuff radicals D or the dyestuffs of this class containing amino groups on which the dyestuffs of the formula (I) are based are described in a very large number in the literature. Examples which may be mentioned here are:
EP-A 54 515, EP-A 69 703, EP-A 70 807, EP-A 497 174, DE-3 222 726, DE-A 2 650 555, DE-A 3 023 855, DE-A 2 847 938, DE-A 2 817 780, GB-A 2 057 479, DE-A 2 916 715, DE-A 2 814 206, DE-A 3 019 936, EP-A 45 488 and Venkataraman: The Chemistry of Synthetic Dyes, Volume VI, Chapter II, pages 211–325, New York, London; 1972.

Preferred radicals of an organic azo dyestuff correspond, for example, to the following groups $$Di\!-\!N\!=\!N\!-\!(M\!-\!N\!=\!N)_{0\ or\ 1}K\!-$$

$$-\!Di\!-\!N\!=\!N\!-\!(M\!-\!N\!=\!N)_{0\ or\ 1}K$$

$$-\!Di\!-\!N\!=\!N\!-\!(M\!-\!N\!=\!N)_{0\ or\ 1}K\!-$$

Di represents the radical of a diazo component of the benzene or naphthalene series which is optionally substituted by substituents customary in azo chemistry, in particular hydroxyl, methyl, ethyl, methoxy or ethoxy groups, optionally substituted alkanoylamino groups having 2–4 C atoms, optionally substituted benzoylamino groups or halogen atoms and $SO_2$—Z, K represents the radical of a coupling component of the benzene, naphthalene or ketomethylene series which is optionally substituted by substituents customary in azo chemistry, in particular hydroxyl, amino, methyl, ethyl, methoxy or ethoxy groups, optionally substituted alkanoylamino groups having 2–4 C atoms, optionally substituted benzoylamino groups or halogen atoms, M represents the radical of a middle component of the benzene or naphthalene series which is optionally substituted by substituents customary in azo chemistry, in particular hydroxyl, methyl, ethyl, methoxy or ethoxy groups, optionally substituted alkanoylamino groups having 2–4 C atoms, optionally substituted benzoylamino groups.or halogen atoms, and Di, M and K together contain at least two sulphonic acid groups, preferably three to four sulphonic acid groups.

Important azo dyestuffs are, for example, those of the benzene-azo-naphthalene series, the bis-(benzene-azo)-naphthalene series, the benzene-azo-5-pyrazolone series, the benzene-azo-benzene series, the naphthalene-azo-benzene series, the benzene-azo-aminonaphthalene series, the naphthalene-azo-naphthalene series, the naphthalene-azo-5-pyrazolone series, the benzene-azo-pyridone series, the benzene-azo-aminopyridine series, the naphthalene-azopyridone series, the naphthalene-azo-amino-pyridine series and the stilbene-azo-benzene series, the dyestuffs containing sulphonic acid groups also being preferred here. In the case of metal complex azo dyestuffs, the metal complex-bonded groups are preferably in the o-position relative to the azo group, for example in the form of o,o'-dihydroxy-, o-hydroxy-o'-carboxy-, o-carboxy-o'-amino- and o-hydroxy-o'-amino-azo groupings.

Preferred dyestuffs are those of the following formulae (9) to (50), wherein, in general, B comprises a radical of the formula

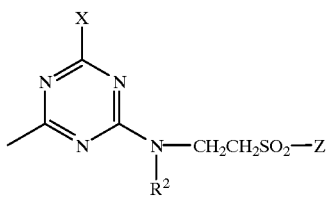

(VIa)

and X, $R^2$ and Z have the meaning given under formula (I):

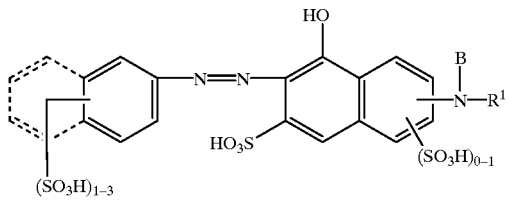

(9)

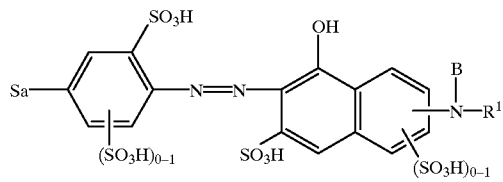

(10)

where Sa = $OCH_3$ or $OC_2H_5$

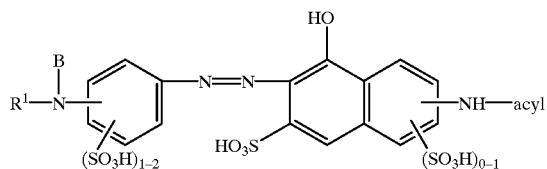

(11)

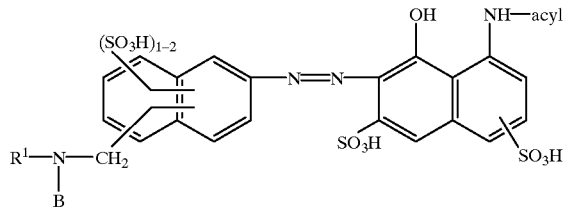

(12)

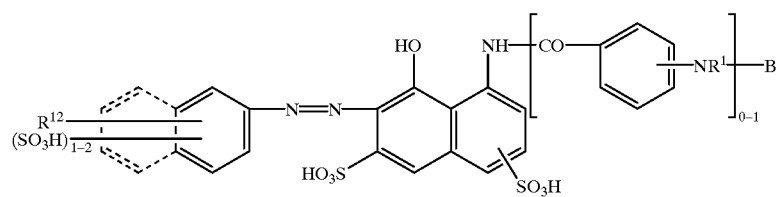

(13)

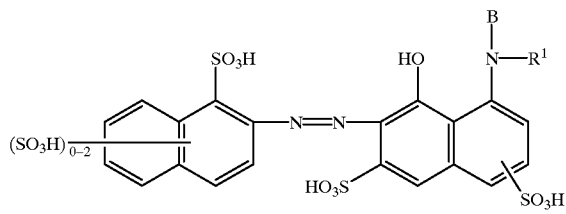

(14)

(15)
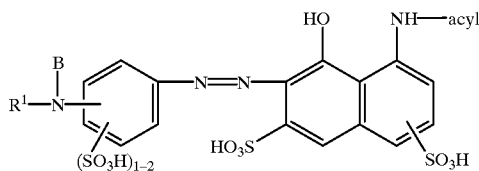
(16)
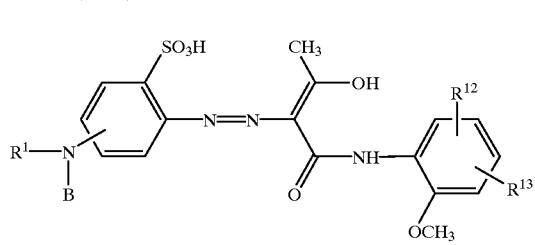
dyestuffs and dyestuffs capable of forming metal complexes of the formulae (20) to (50):
(20)
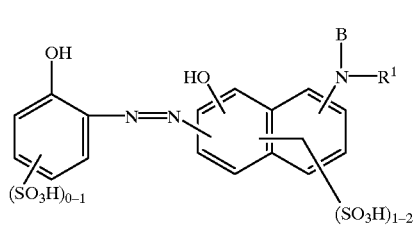
(21)
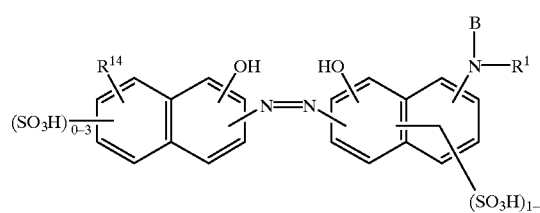
(22)
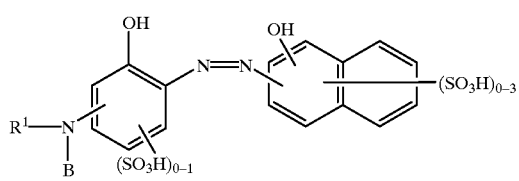
(23)
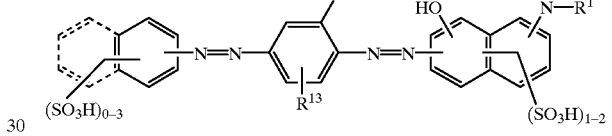
(24)
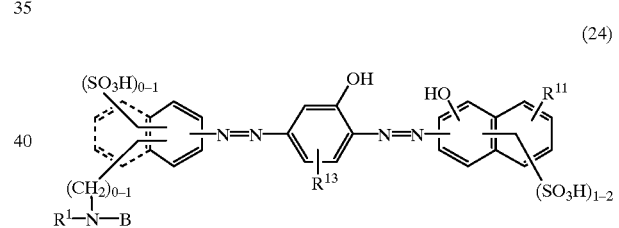
Cu (1:1 complex) or Cr and Co (1:2 complex) are the preferred metal atom. Cr and Co complexes can contain the azo compound of the abovementioned formula once or twice, that is to say they can be built up symmetrically or unsymmetrically with any other desired ligand groups.
(25)
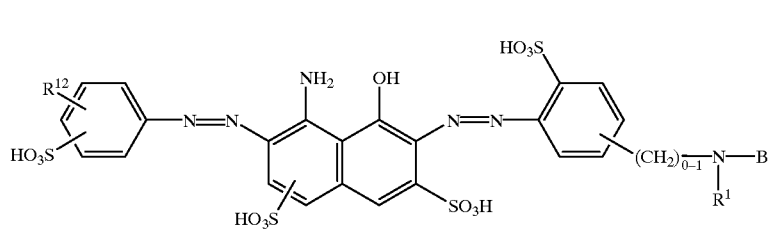

-continued
(26)
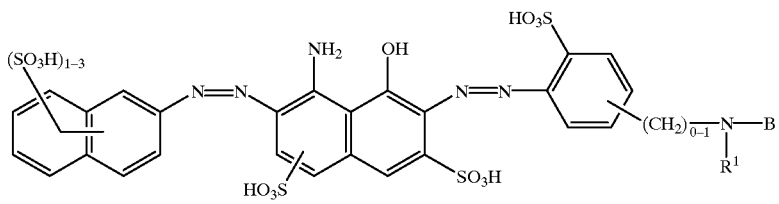
(27)
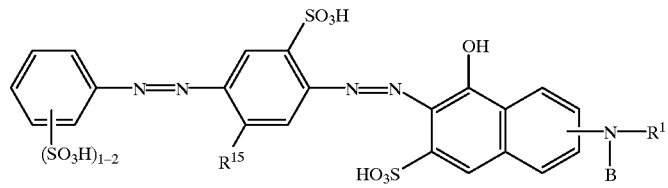
(28)
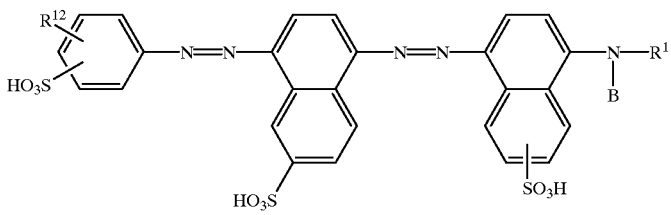
(29)
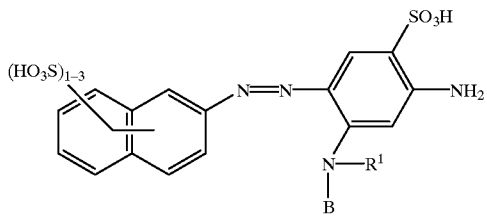
(30)
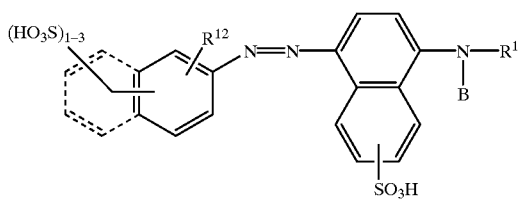
(31)
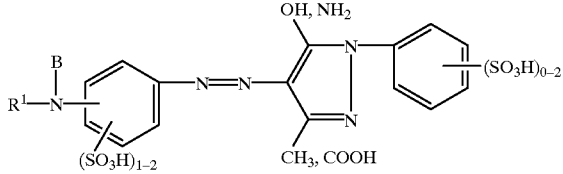
(32)
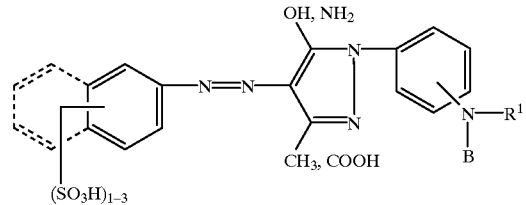

-continued
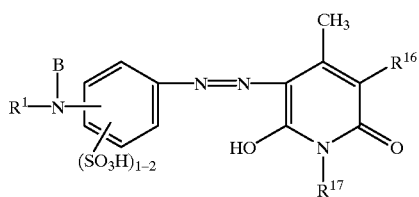
(33)
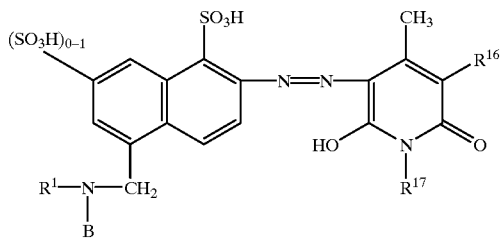
(34)
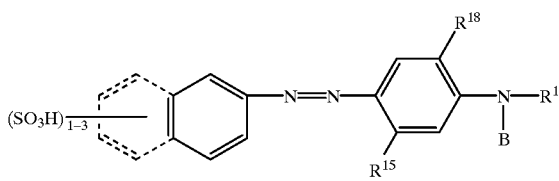
(35)
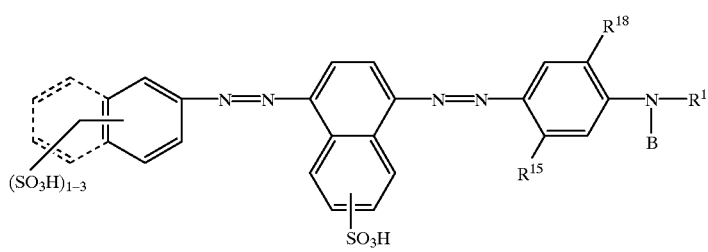
(36)
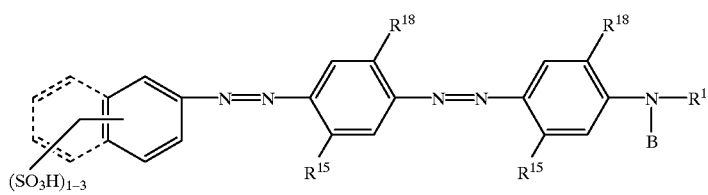
(37)
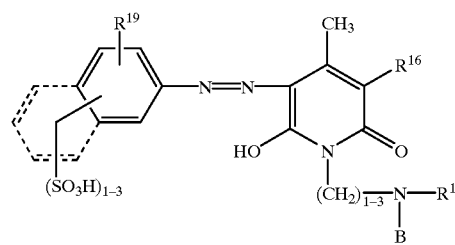
(38)
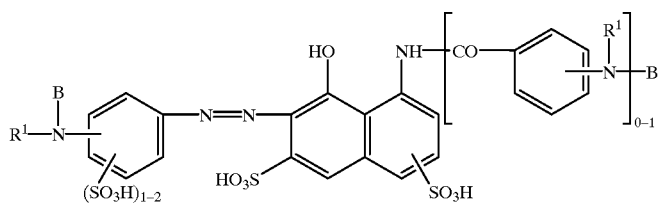
(39)

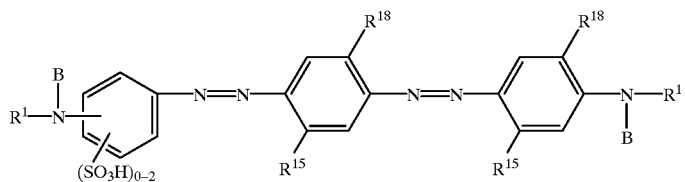
(40)
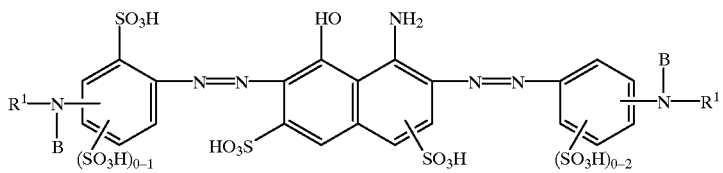
(41)
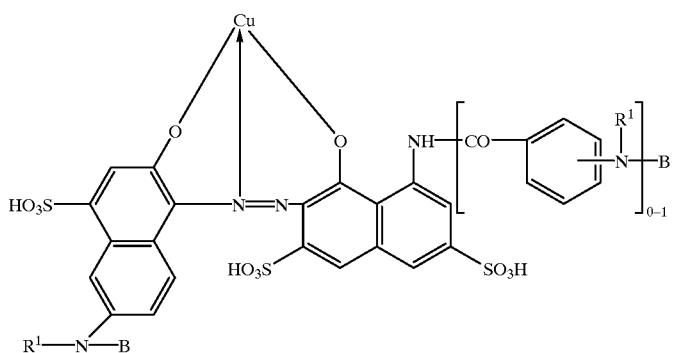
(42)
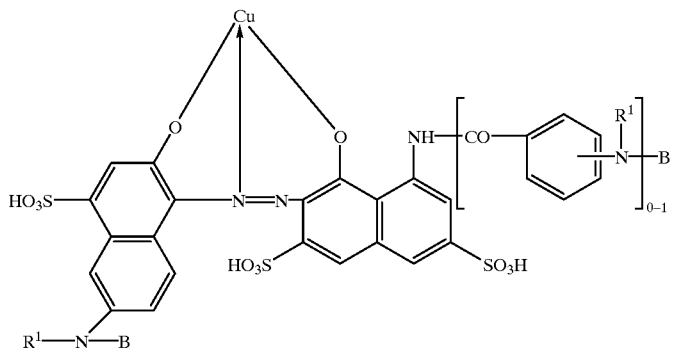
(43)
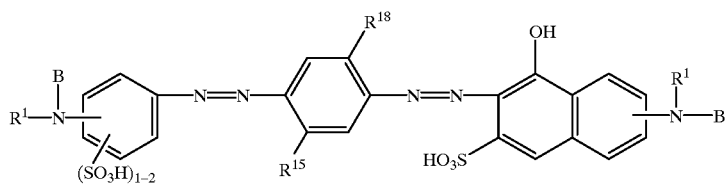
(44)

(45)
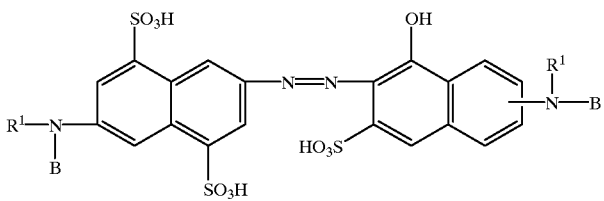

(46)
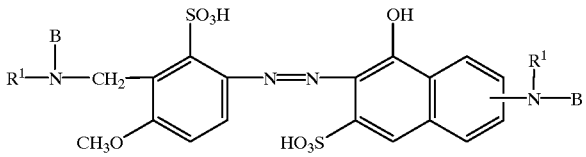

(47)
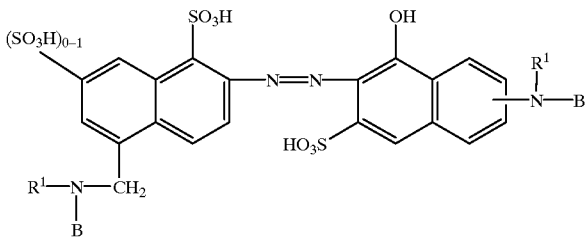

(48)
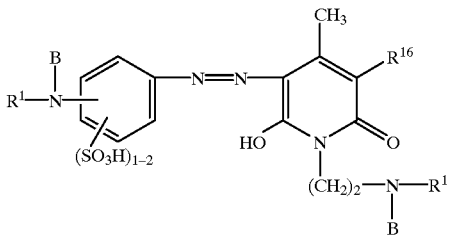

(49)
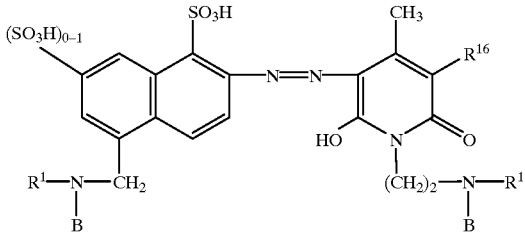

(50)
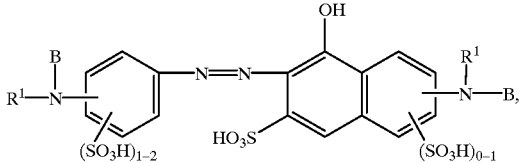

wherein
- acyl is, for example, acetyl or optionally substituted benzoyl,
- $R^{17}$=H or $C_1$–$C_2$-alkyl, optionally substituted by $SO_3H$ or $NH_2$,
- $R^1$=H, $CH_3$ or $C_2H_5$,
- $R^{19}$=H or sulpho,
- $R^{13}$=H, $CH_3$, $OCH_3$ or Cl,
- $R^{12}$=H, $C_1$–$C_4$-alkyl, $C_1$–$C_4$-alkoxy, Cl, Br, COOH or $SO_3H$,
- $R^{14}$=H, OH, $NH_2$, $NHCOCH_3$, NHCOPh, Cl, $C_1$–$C_4$-alkoxy or $C_1$–$C_4$-alkyl,
- $R^{16}$=H, $SO_3H$, $CH_2SO_3H$, Cl, $C_1$–$C_4$-alkylsulphonyl, CN or carboxamide, in particular $CONH_2$,
- $R^{15}$=H, $C_1$–$C_4$-alkyl, $C_1$–$C_4$-alkoxy, Cl, Br or acylamino, in particular $C_1$–$C_4$-alkylcarbonylamino or arylcarbonylamino, such as optionally substituted phenyl carbonylamino, $C_1$–$C_4$-alkylsulphonylamino, amino carbonylamino, $C_1$–$C_4$-alkylsulphonylamino or arylsulphonylamino,
- $R^{18}$=H, $C_1$–$C_4$-alkyl, $C_1$–$C_4$-alkoxy, OH or $SO_3H$.

The fused rings indicated by broken lines represent alternatively possible naphthalene systems.

Preferred reactive dyestuffs are furthermore those of the formula (I)
wherein
the radical D, preferably a radical of an organic dyestuff from the monoazo or polyazo series, is substituted once or twice by the group

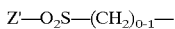

wherein
Z' denotes —CH=CH$_2$, —CH$_2$—CH$_2$—OSO$_3$H, —CH$_2$—CH$_2$—Cl, —CH$_2$—CH$_2$—Br, —CH$_2$—CH$_2$—S$_2$O$_3$H, —CH$_2$—CH$_2$—O—CO—CH$_3$, —CH$_2$—CH$_2$—OPO$_3$H$_2$ or —CH$_2$—CH$_2$—OH.

Particularly preferred reactive dyestuffs of the formula (I) are those
wherein
the radical D, preferably a radical of an organic dyestuff from the monoazo or polyazo series, is substituted once or twice by the group

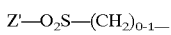

wherein
Z' has the above meaning and n=1.

Reactive dyestuffs of the formula (I) which are furthermore particularly preferred are those in which
n=1,
W=a direct bond and
D is a radical of the general formula (IX)

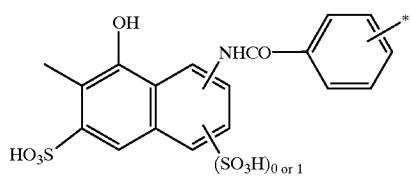

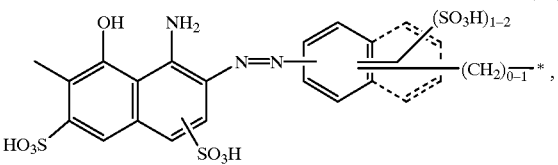

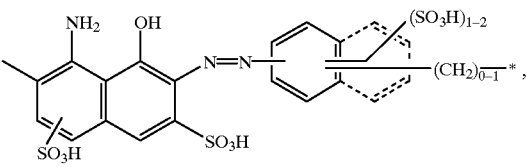

and where the bonds identified with * are bonded to the group —NR$^1$—B. B has the meaning of formula (VIa).

Z' particularly preferably denotes —CH=CH$_2$ or —C$_2$H$_4$—OSO$_3$H.

Suitable diazo components, on which the radicals D of the formula (IX) are based, for the dyestuffs of the formulae (I) are, for example:
aniline-4-β-sulphatoethylsulphone,

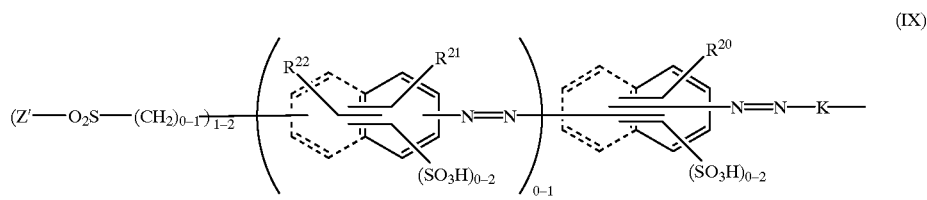

wherein

R$^{20}$ denotes H, C$_1$–C$_4$-alkyl, C$_1$–C$_4$-alkoxy, Cl, Br, acylamino, in particular C$_1$–C$_4$-alkylcarbonylamino or arylcarbonylamino, such as optionally substituted phenylcarbonylamino, C$_1$–C$_4$-alkyl-sulphonylamino, amimocarbonylamino, C$_1$–C$_4$-alkyl-sulphonylamino or arylsulphonylamino, R$^{21}$ denotes H, C$_1$–C$_4$-alkyl, Cl, Br, C$_1$–C$_4$-alkoxy or COOH, R$^{22}$ denotes H, C$_1$–C$_4$-alkyl, C$_1$–C$_4$-alkoxy, SO$_3$H, Cl or Br, K denotes a bivalent radical of the general formulae (Xa)–(Xd)

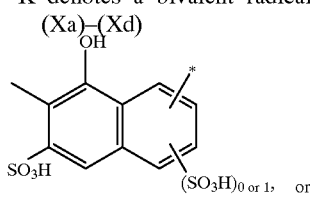

aniline-4-β-thiosulphatoethylsulphone,
aniline-4-vinylsulphone,
aniline-3-β-sulphatoethylsulphone,
aniline-3-vinylsulphone,
2-methoxy-aniline-5-β-sulphatoethylsulphone,
2-methoxy-aniline-5-β-thiosulphatoethylsulphone,
2-methoxyaniline-5-vinylsulphone,
4-methoxy-aniline-3-β-sulphatoethylsulphone,
4-methoxy-aniline-3-β-vinylsulphone,
2,5-dimethoxyaniline-4-β-sulphatoethylsulphone,
2,5-dimethoxy-aniline-4-vinylsulphone,
2-methoxy-5-methyl-aniline-4-β-sulphatoethylsulphone,
aniline-2-β-sulphatoethylsulphone,
3-(3- or 4-aminobenzoyl)-aminophenyl-β-sulphatoethylsulphone,
2-methoxy-5-methyl-aniline-4-vinylsulphone,
6-carboxy-aniline-3-β-sulphatoethylsulphone,
6-carboxyaniline-3-vinylsulphone,
2-sulphoaniline-4-β-sulphatoethylsulphone,
2-sulphoaniline-4-vinylsulphone,
2,4-disulphoaniline-5-vinylsulphone,
2-naphthylamine-8-β-sulphatoethylsulphone,
2-naphthylamine-6-β-sulphatoethylsulphone, 1-sulpho-2-naphthylamine-6-β-sulphatoethylsulphone,
1-naphthylamine-4-β-sulphatoethylsulphone,
1-sulpho-2-naphthylamine-5-β-sulphatoethylsulphone,
6-sulpho-2-naphthylamine-8-β-sulphatoethylsulphone,
2-amino-3-sulpho-naphthalene-6,8-bis (β-sulphatoethyl-sulphone),
1-naphthylamine-5-β-sulphatoethylsulphone,
2-naphthylamine-5-β-sulphatoethylsulphone,
2-naphthylamine-8-β-suphatoethylsulphone,
8-sulpho-2-naphthylamine-6-β-sulphatoethylsulphone,
4-aminobenzyl-β-sulphatoethylsulphone,
3-aminobenzyl-β-sulphatoethylsulphone,
4-aminobenzylvinylsulphone,
3-aminobenzylvinylsulphone,
3-amino-4-sulphobenzyl-β-sulphatoethylsulphone,
4-amino-3-sulphobenzylvinylsulphone,
2'-(β-sulphatoethylsulphonyl)-3-sulpho-4-amino-azobenzene,
3'-(β-sulphatoethylsulphonyl)-3-sulpho-4-amino-azobenzene,
4'-methoxy-3'-(β-sulphatoethylsulphone)-3-sulpho-4-aminoazobenzene,
4'-vinylsulphonyl-2',3-disulpho-4-aminoazobenzene,
2'-(β-sulphatoethylsulphonyl)-6-methyl-3-sulpho-4-amino-azobenzene,
3'-(β-sulphatoethylsulphonyl)-6-methyl-3-sulpho-4-amino-azobenzene,
4'-(β-sulphatoethylsulphonyl)-6-methyl-3-sulpho-4-amino-azobenzene,
4'-(β-sulphatoethylsulphonyl)-2,6-dimethyl-3-sulpho-4-aminoazobenzene,
3'-(β-sulphatoethylsulphonyl)-6-methoxy-3-sulpho-4-aminoazobenzene,
3',4'-bis-(β-sulphatoethylsulphonyl)-6-methoxy-3-sulpho-4-aminoazobenzene,
4'-(β-sulphatoethylsulphonyl)-6-methoxy-3-sulpho-4-aminoazobenzene,
4'-(β-sulphatoethylsulphonyl)-2-methyl-5-methoxy-3-sulpho-4-aminoazobenzene,
4'-(β-sulphatoethylsulphonyl)-2,5-dimethoxy-3-sulpho-4-aminoazobenzene,
3'-(β-sulphatoethylsulphonyl)-2,5-dimethoxy-3-sulpho-4-aminoazobenzene,
2-(4'-amino-3'-sulphophenylazo)-6-(β-sulphatoethylsulphonyl)-naphthalene,
2-(4'-amino-6'-methyl-3'-sulphophenylazo)-1-sulpho-6-(β-sulphatoethylsulphonyl)-naphthalene,
2-(4'-amino-6'-methyl-3'-sulphophenylazo)-6-(β-sulphatoethylsulphonyl)-naphthalene,
2-(4'-amino-3'-sulphophenylazo)-8-sulpho-6-(β-sulphatoethylsulphonyl)-naphthalene,
2-(4'-amino-6'-methyl-3'-sulphophenylazo)-1,7-disulpho-5-(β-sulphatoethylsulphonyl)-naphthalene.

Suitable coupling components H-K-NHR¹ on which the radicals K are based are, for example:

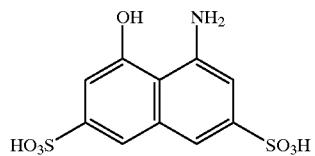

-continued

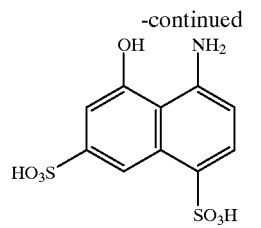

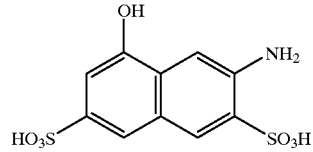

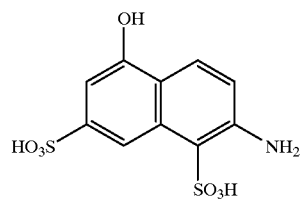

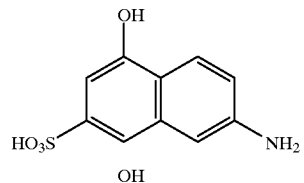

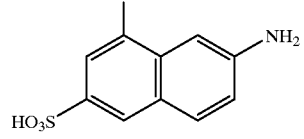

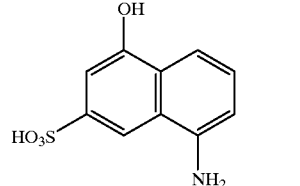

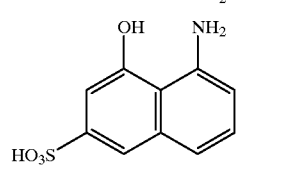

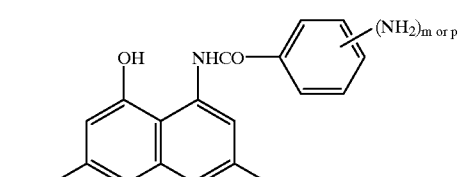

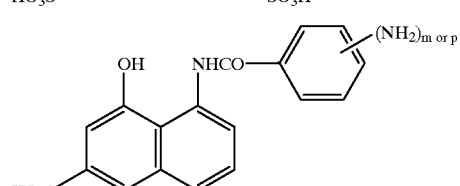

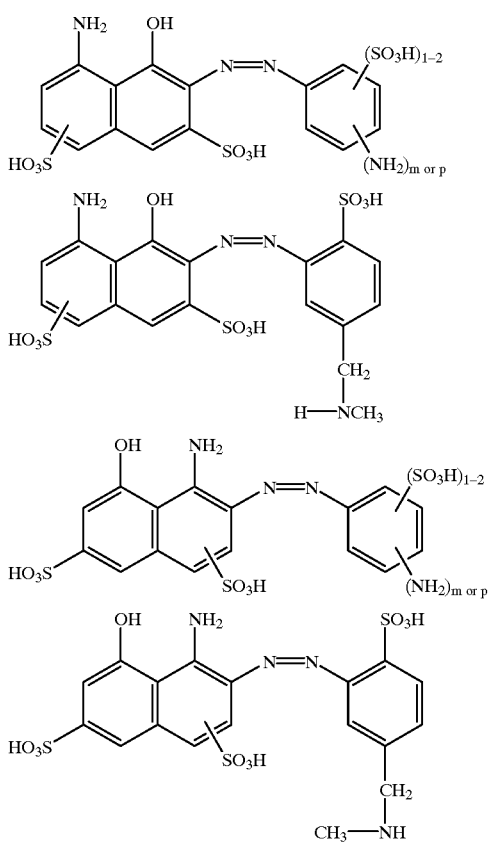
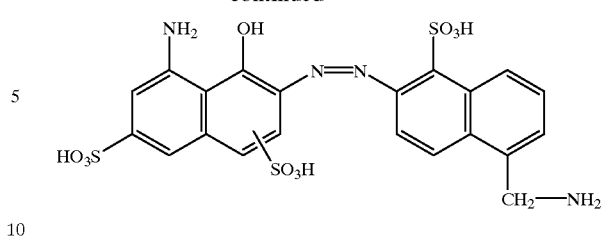
where * marks the coupling site and m and p represent the meta- and para-position of the amino group relative to the azo group.
Preferred dyestuffs in the context of formula I: with a dyestuff radical D of the formula (IX) are those of the following formulae (51) to (60), wherein, in general, B comprises a radical of the formula
(VIa)
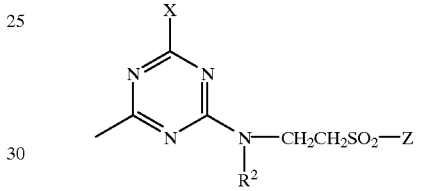
and X, $R^2$ and Z have the abovementioned meaning:
(51)
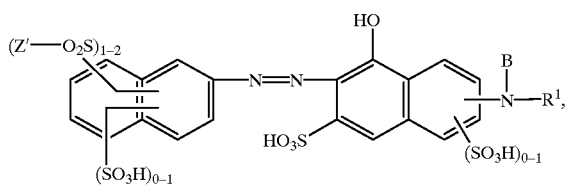
(52)
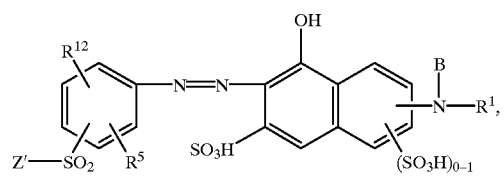
(53)
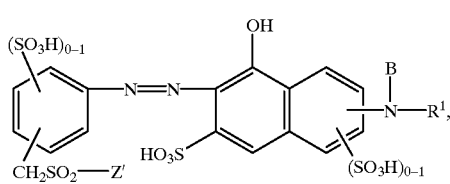
(54)
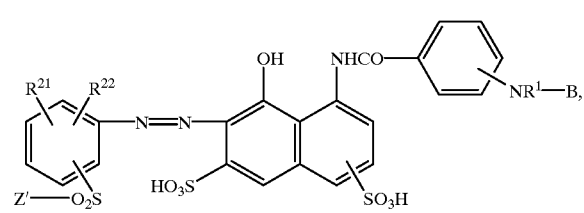
(55)
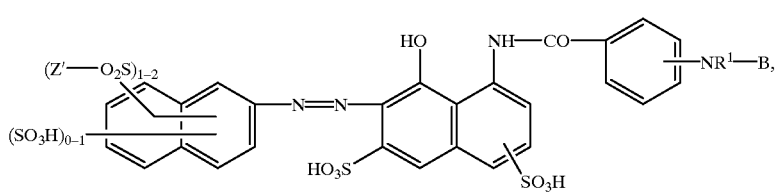

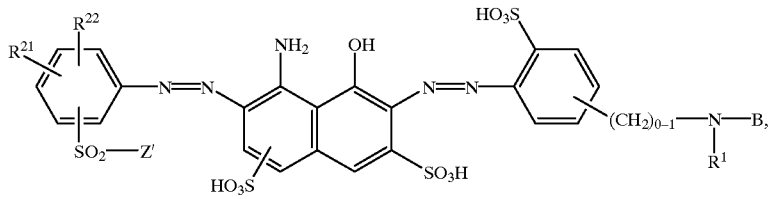
(56)

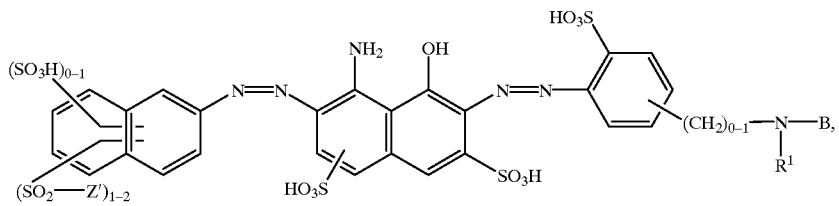
(57)

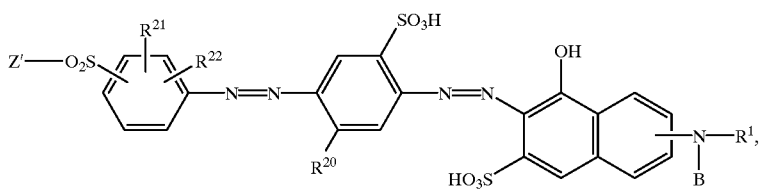
(58)

wherein $R^1$=H, $CH_3$ or $C_2H_5$, $R^{20}$=H, $C_1$–$C_4$-alkyl, $C_1$–$C_4$-alkoxy, Cl, Br, acylamino, in particular $C_1$–$C_4$-alkylcarbonylamino or arylcarbonylamino, such as optionally substituted phenylcarbonylamino, $C_1$–$C_4$-alkylsulphonylamino, aminocarbonylamino, $C_1$–$C_4$-alkylsulphonylamino or arylsulphonylamino, $R^{21}$=H, $C_1$–$C_4$-alkyl, $C_1$–$C_4$-alkoxy, Cl, Br or COOH, $R^{22}$=H, $C_1$–$C_4$-alkyl, $C_1$–$C_4$-alkoxy, Cl, Br or $SO_3H$.

Dyestuffs of this series which are likewise particularly useful are reactive dyestuffs of the formula

(XI)

DK=the radical of a diazo component of the benzene or naphthalene series,

KK=the radical of a coupling component of the formula

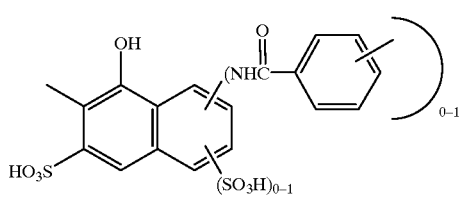
(XII)

wherein the radical of the formula XII and the azo group are linked to one another via the bond marked with *, B=a radical of the formula

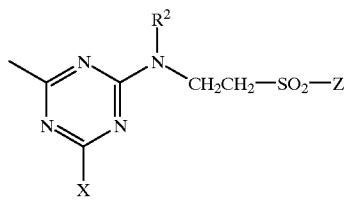
(VIa)

Y=a heterocyclic fibre-reactive radical which differs from B, $R^0$ and $R^1$=independently of one another H or $C_1$–$C_6$-alkyl which is optionally substituted with substituents such as, for example, OH, COOH, $SO_3H$ or $OSO_3H$, and $R^2$, X and Z have the above meaning.

Suitable fibre-reactive radicals Y, that is to say those which react with the OH or NH groups of fibres under dyeing conditions to form covalent bonds, are preferably those which contain at least one reactive substituent bonded to a 5- or 6-membered aromatic-heterocyclic ring, for example to a monoazine, diazine or triazine ring, in particular a pyridine, pyrimidine, pyridazine, thiazine, oxazine or asymmetric or symmetric triazine ring, or to such a ring system which contains one or more fused-on aromatic-carbocyclic rings, for example a quinoline, phthalazine, cinnoline, quinazoline, quinoxaline, acridine, phenazine or phenanthridine ring system, and which are not bonded to a further chromophore.

Reactive substituents on the heterocyclic ring which may be mentioned are, for example, halogen (Cl, Br or F), ammonium, including hydrazinium, pyridinium, picolinium, carboxypyridinium, sulphonium, sulphonyl, azido($N_3$), thiocyanato, thioether, oxy-ether, sulphinic acid and sulphonic acid.

Specifically, for example, the following radicals may be mentioned for Y:

2,4-Difluorotriazin-6-yl, 2,4-dichlorotriazin-6-yl and mono-halogeno-sym.-triazinyl radicals, in particular monochloro- and monofluorotriazinyl radicals which are substituted by alkyl, aryl, amino, monoalkylamino, dialkylamino, aralkylamino, arylamino, morpholino, piperidino, pyrrolidino, piperazino, alkoxy, aryloxy, alkylthio or arylthio, where alkyl preferably denotes optionally substituted $C_1$–$C_4$-alkyl, aralkyl preferably denotes optionally substituted phenyl-$C_1$–$C_4$-alkyl and aryl preferably denotes optionally substituted phenyl or naphthyl, and where preferred substituents for alkyl are halogen, hydroxyl, cyano, dialkylamino, morpholino, $C_1$–$C_4$-alkoxy, carboxyl, sulpho or sulphato and preferred substituents for phenyl and naphthyl are sulpho, $C_1$–$C_4$-alkyl, $C_1$–$C_4$-alkoxy, carboxyl, halogen, acylamino, hydroxyl and amino. Radicals which may furthermore be mentioned are 2-amino-4-fluorotriazin-6-yl, 2-methyl-amino-4-fluorotriazin-6-yl, 2-ethylamino-4-fluorotriazin-6-yl, 2-isopropylamino-4-fluoro-triazin-6-yl, 2-dimethyl-amino-4-fluorotriazin-6-yl, 2-diethylamino-4-fluoro-triazin-6-yl, 2-β-methoxy-ethylamino-4-fluoro-triazin-6-yl, 2-β-hydroxyethylamino-4-fluoro-triazin-6-yl, 2-di-(β-hydroxy-ethylamino)-4-fluoro-triazin-6-yl, 2-carboxy-methylamino-4-fluoro-triazin-6-yl, 2-di-(carboxymethylamino)-4-fluoro-triazin-6-yl, 2-sulphomethyl-methyl-amino-4-fluoro-triazin-6-yl, 2-β-cyanoethylamino-4-fluoro-triazin-6-yl, 2-benzylamino-4-fluoro-triazin-6-yl, 2-β-phenylethylamino-4-fluoro-triazin-6-yl, 2-benzyl-methyl-amino-4-fluoro-triazin-6-yl, 2-(4'-sulphobenzyl)-amino-4-fluoro-triazin-6-yl, 2-cyclohexylamino-4-fluoro-triazin-6-yl, 2-(o-, m-, p-methylphenyl)-amino-4-fluoro-triazin-6-yl, 2-(o-, m-, p-sulphophenyl)-amino-4-fluoro-triazin-6-yl, 2-(2',5'-disulphophenyl)-amino-4-fluoro-triazin-6-yl, 2-(o-, m-, p-chlorophenyl)-amino-4-fluoro-triazin-6-yl, 2-(o-, m-, p-methoxyphenyl)-amino-4-fluoro-triazin-6-yl, 2-(2'-methyl-4'-sulphophenyl)-amino-4-fluoro-triazin-6-yl, 2-(2'-methyl-5'-sulphophenyl)-amino-4-fluoro-triazin-6-yl, 2-(2'-chloro-4'-sulphophenyl)-amino-4-fluoro-triazin-6-yl, 2-(2'-chloro-4'-sulphophenyl)-amino-4-fluoro-triazin-6-yl, 2-(2'-methoxy-4'-sulphophenyl)-amino-4-fluoro-triazin-6-yl, 2-(o-, m-, p-carboxyphenyl-)-amino-4-fluoro-triazin-6-yl, 2-(2'-,4'-disulphophenyl-)-amino-4-fluoro-triazin-6-yl, 2-(3'-,5'-disulphophenyl)-amino-4-fluoro-triazin-6-yl, 2-(2'-carboxy-4'-sulphophenyl)-amino-4-fluoro-triazin-6-yl, 2-(2'-carboxy-5'-sulphophenyl)-amino-4-fluoro-triazin-6-yl, 2-(6'-sulphonaphth-2'-yl)-amino-4-fluoro-triazin-6-yl, 2-(4',8'-disulphonaphth-2'-yl)-amino-4-fluoro-triazin-6-yl, 2-(6',8'-disulphonaphth-2'-yl)-amino-4-fluoro-triazin-6-yl, 2-(N-methyl-N-phenyl)-amino-4-fluoro-triazin-6-yl, 2-(N-ethyl-N-phenyl)-amino-4-fluoro-triazin-6-yl, 2-(N-β-hydroxyethyl-N-phenyl)-amino-4-fluoro-triazin-6-yl, 2-(N-iso-propyl-N-phenyl)-amino-4-fluoro-triazin-6-yl, 2-morpholino-4-fluoro-triazin-6-yl, 2-piperidino-4-fluoro-triazin-6-yl, 2-(4',6',8'-trisulphonaphth-2'-yl)-amino-4-fluoro-triazin-6-yl, 2-(3',6',8'-trisulphonaphth-2'-yl)-amino-4-fluoro-triazin-6-yl, 2-(3',6'-disulphonaphth-1'-yl)-amino-4-fluoro-triazin-6-yl, N-methyl-N-(2-methyl-amino-4-chlorotriazin-6-yl)-carbamyl, N-methyl-N-(2-dimethylamino-4-chlorotriazin-6-yl)-carbamyl, N-methyl- or N-ethyl-N-(2,4-dichlorotriazinyl-6)-amino-acetyl, 2-methyloxy-4-fluoro-triazin-6-yl, 2-ethoxy-4-fluoro-triazin-6-yl, 2-phenoxy-4-fluoro-triazin-6-yl, 2-(o-, m- or p-methyl or -methoxy-phenoxy)-4-fluoro-triazin-6-yl, 2-β-hydroxy-ethylmercapto-4-fluoro-triazin-6-yl, 2-phenylmercapto-4-fluoro-triazin-6-yl, 2-(4'-methylphenyl)-mercapto-4-fluorotriazin-6-yl, 2-(2',4'-dinitrophenyl)-mercapto-4-fluoro-triazin-6-yl, 2-methyl-4-fluoro-triazin-6-yl, 2-phenyl-4-fluoro-triazin-6-yl and the corresponding 4-chloro- and 4-bromo-triazinyl radicals and the corresponding radicals obtainable by replacement of halogen with tertiary bases, such as trimethylamine, triethylamine, dimethyl-β-hydroxyethylamine, triethanolamine, N,N-dimethylhydrazine, pyridine, α-, β- or γ-picoline, nicotinic acid or isonicotinic acid, sulphinates, in particular benzenesulphinic acid, or hydrogen sulphite, as well as di- or trihalogenopyrimidine radicals, such as 2,4-dichloropyrimidin-6-yl, 2,4,5-trichloropyrimidin-6-yl, 4,5-dichloropyrimidin-6-yl, 2,4-difluoropyrimidin-6-yl and 4,5-difluoro-5-chloropyrimidyl, as well as 2,3-dichloroquinoxaline-5-carbonyl and 2,3-dichloroquinoxaline-6-carbonyl.

The reactive dyestuffs of the formula (XI) have two possible forms

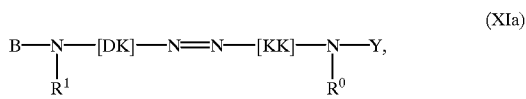

(XIa)

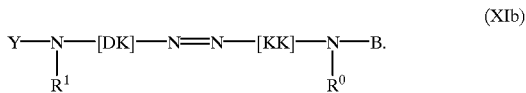

(XIb)

Preferred reactive dyestuffs of the formula (XI) are those wherein

KK denotes a bivalent radical of a coupling component of the general formula

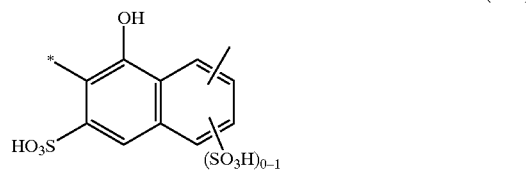

(XIIa)

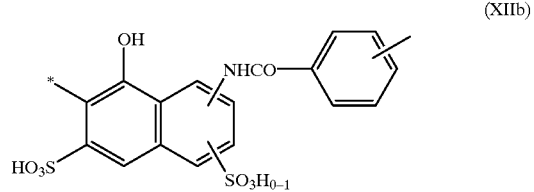

(XIIb)

where the radical (XIIa) or (XIIb) and the azo group are linked to one another via the bond marked with *, DK denotes a radical of a diazo component of the general formula

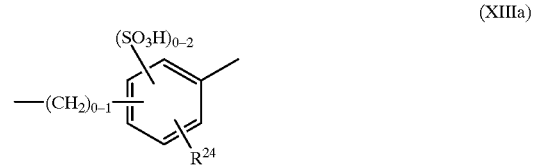

(XIIIa)

-continued

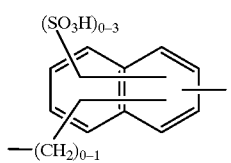
(XIIIb)

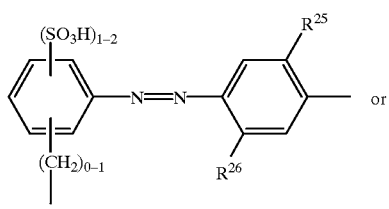
(XIIIc)
or

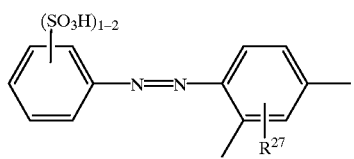
(XIIId)

and
$R^{25}$=H, $C_1$–$C_4$-alkyl, $C_1$–$C_4$-alkoxy, OH or $SO_3H$,
$R^{26}$=H, $C_1$–$C_4$-alkyl, $C_1$–$C_4$-alkoxy, acylamino, in particular $C_1$–$C_4$-alkylcarbonylamino, $C_1$–$C_4$-alkylsulphonylamino or aminocarbonylamino,
$R^{24}$ and $R^{27}$=independently H, $CH_3$, $C_2H_5$ or $OCH_3$ and B, R, Y and $R^1$ have the abovementioned meanings.

Reactive dyestuffs according to the invention which are furthermore preferred are those of the formula (XI) or (XIa–XIb), wherein Y denotes a fibre-reactive fluorine-containing pyrimidin-6-yl radical or a radical of the formula

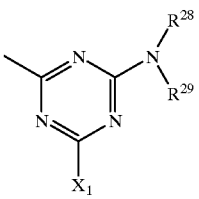
(XIV)

wherein $R^{28}$ and $R^{29}$ independently of one another denote H, $C_1$–$C_4$-alkyl and $C_5$–$C_6$-cycloalkyl which are optionally substituted by substituents such as, for example, halogen, cyano, $C_1$–$C_4$-alkoxy, hydroxyl, phenyl, carboxyl, sulpho or sulphato, for example benzyl, phenethyl or cyclohexyl, or $C_6$–$C_{10}$-aryl, in particular phenyl or naphthyl, which is [lacuna] substituted [lacuna] such as halogen, nitro, cyano, trifluoromethyl, sulphamoyl, carbamoyl, $C_1$–$C_4$-alkyl, $C_1$–$C_4$-alkoxy, $C_1$–$C_4$-alkanoylamino, benzoylamino, ureido, hydroxyl, carboxyl, sulphomethyl or sulpho, or wherein $R^{28}$ and $R^{29}$, together with the amino nitrogen atom, form a morpholino, piperidino or piperazino radical, and wherein $X_1$=Cl, F or a pyridinium radical which is optionally substituted by, for example, COOH or $SO_3H$.

Particularly preferred reactive dyestuffs are those of the formulae (61)–(72)

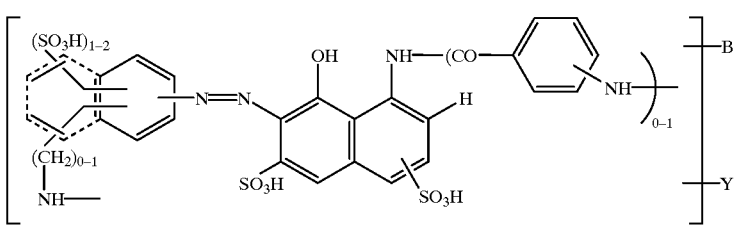
(61)

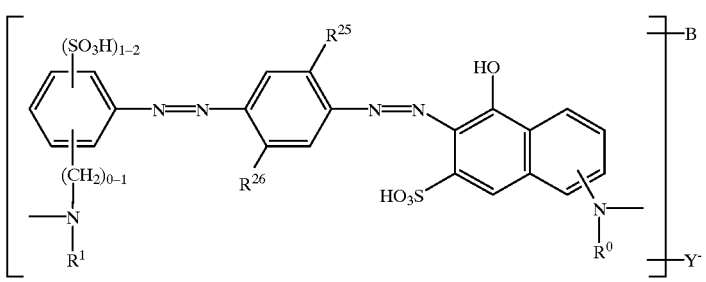
(62)

(63)

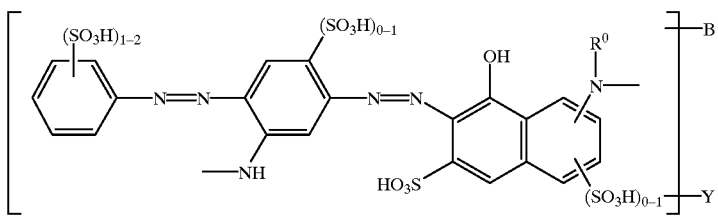
(64)
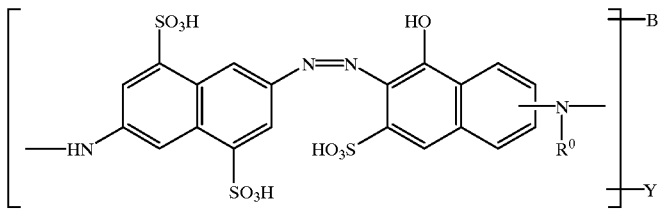
(65)
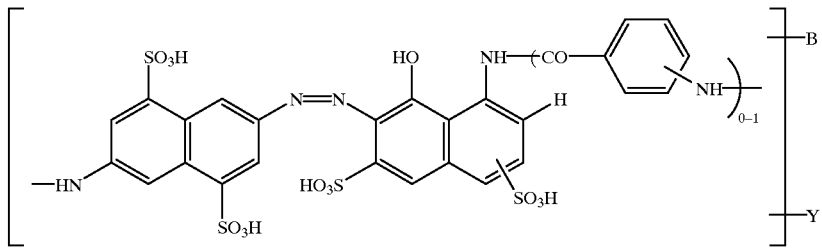
(66)
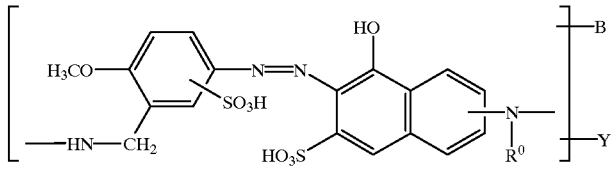
(67)
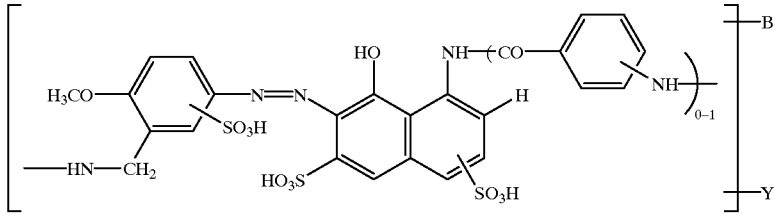
(68)
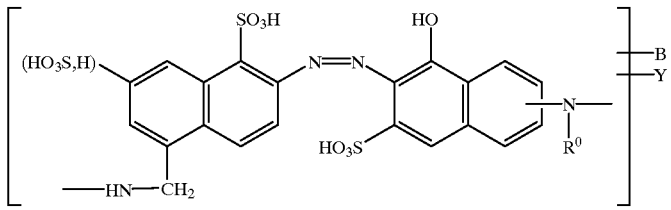
(69)

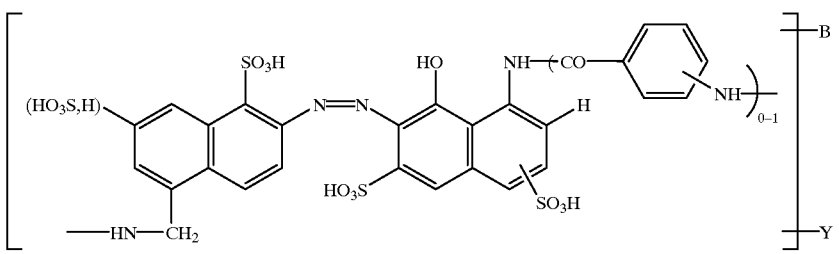

(70)

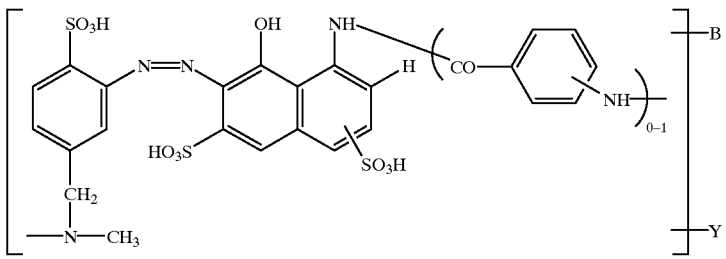

(71)

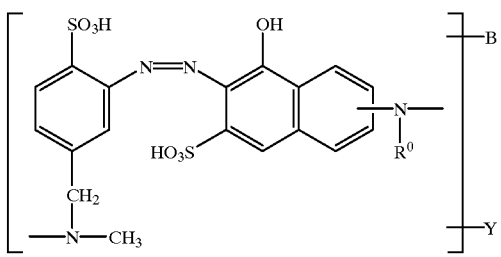

(72)

wherein
$R^0$=H, $CH_3$ or ethyl and
$R^1$, $R^{25}$, $R^{26}$, B and Y have the abovementioned meaning.

Reactive dyestuffs of the formula (61) to (72) which are particularly preferred above all are those wherein Y is a fluoro-s-triazine radical substituted by —$NR^{28}R^{29}$ wherein —$NR^4R^5$ preferably represents: —$NH_2$, morpholino, N-β-hydroxyethylamino, N,N-di-β-hydroxyethylamino, β-sulphoethylamino, phenylamino, which is optionally substituted on the phenyl nucleus by chlorine, methyl, ethyl, methoxy, ethoxy, acetylamino, hydroxyl, carboxyl, sulphomethyl or sulpho, N-$C_{1-4}$-alkyl-phenylamino, which is optionally substituted on the phenyl nucleus by chlorine, methyl or ethyl, N-(sulpho-$C_{1-4}$-alkyl)-phenylamino, which is optionally substituted on the phenyl nucleus by chlorine, methyl or ethyl, N-(hydroxy-$C_{1-4}$-alkyl)-phenylamino or sulphonaphthylamino.

The invention furthermore relates to a process for the preparation of reactive dyestuffs of the formula (XI), characterized in that dyestuffs of the formula (XV)

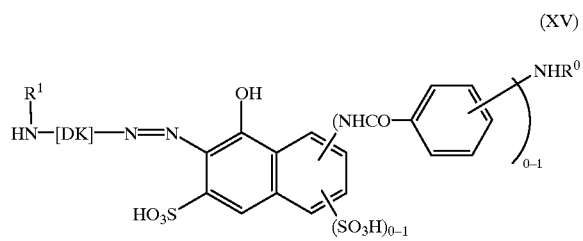

are reacted in any desired sequence with in each case one molar equivalent of the reactive component of the formula

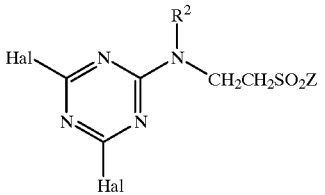

(XVI)

and of the reactive component of the formula

Y-Hal     (VIII)

or in that the corresponding dyestuff precursors of the formulae $R^1$—NH—[DK]—$NH_2$ and H—[KK]—NHR are each reacted with in each case one molar equivalent of the reactive component of the formula (VII) or (VIII) and the products are converted by diazotization and coupling, and if appropriate further conversion reactions, into the reactive dyestuffs of the formula (I), wherein the meaning of the radicals R, $R^1$, $R^2$, Hal, B, p and M corresponds to that given above.

In the preparation of the preferred azo dyestuffs, the diazo component and the coupling component together have two amino groups —N($R^0$)H and —N($R^1$)H, and if appropriate other acylatable amino groups. If appropriate, corresponding acetylamino or nitro compounds are used, wherein the acetylamino or nitro group is converted into the $NH_2$ group by hydrolysis or reduction before the condensation with a halogenotriazine, halogenopyrimidine or the like. The reactive radicals B and Y are introduced by condensation of dyestuffs or dyestuff precursors which contain acylatable amino groups with fibre-reactive halogenated acylating agents.

Since the individual process steps described above can be carried out in different sequences, various process variants are possible. In general, the reactions are carried out stepwise in succession, the sequence of the simple reactions between the individual reaction components advantageously depending on the particular conditions.

Since hydrolysis of a halogenotriazine or halogenopyrimidine radical and the like occurs under certain preconditions, an intermediate product which contains acetylamino groups must be hydrolysed in order to split off the acetyl groups before the condensation with an aminodifluorotriazine or trifluorotriazine and the like is carried out. Another possible conversion reaction is, for example, subsequent reaction of a dihalogenotriazinyl radical with an amine. Which reaction is expediently carried out first in the preparation of a secondary condensation product of amine $HNR^{25}R^{29}$, 2,5,6-trihalogeno-s-triazine and diaminobenzenesulphonic acid, that of the trihalogenotriazine with the amine or with the diaminobenzenesulphonic acid, differs from case to case and depends above all on the solubility of the amino compounds participating and the basicity of the amino groups to be acylated. The most important process variants are described in the embodiment examples.

Suitable starting compounds for the preparation of mono- or polyazo dyestuffs (XI) are, for example:

Diazo Components ($R^1$—NH—[DK]—$NH_2$)

1,3-Diaminobenzene, 1,4-diaminobenzene, 1,3-diamino-4-methylbenzene, 1,3-diamino-4-ethylbenzene, 1,3-diamino-4-methoxybenzene, 1,3-diamino-4-ethoxybenzene, 1,4-diamino-2-methylbenzene, 1,4-diamino-2-methoxybenzene, 1,4-diamino-2-ethoxybenzene, 1,4-diamino-2,5-dimethylbenzene, 1,4-diamino-2,5-diethylbenzene, 1,4-diamino-2-methyl-5-methoxybenzene, 1,4-diamino-2,5-dimethoxybenzene, 1,4-diamino-2,5-diethoxybenzene, 2,6-diamino-naphthalene, 1,3-diamino-2,4,6-trimethylbenzene, 1,4-diamino-2,3,5,6-tetramethylbenzene, 1,3-diamino-4-nitrobenzene, 4,4'-diaminostilbene, 4,4'-diaminodiphenylmethane, 2,6-diaminonaphthalene-4,8-disulphonic acid, 1,4-diaminobenzene-2-sulphonic acid, 1,4-diaminobenzene-2,5-disulphonic acid, 1,4-diaminobenzene-2,6-disulphonic acid, 1,3-diaminobenzene-4-sulphonic acid, 1,3-diaminobenzene-4,6-disulphonic acid, 1,4-diamino-2-methylbenzene-5-sulphonic acid, 1,5-diamino-6-methylbenzene-3-sulphonic acid, 1,3-diamino-6-methylbenzene-4-sulphonic acid, 3-(3'- or 4'-aminobenzoylamino)-1-aminobenzene-6-sulphonic acid, 1-(4'-aminobenzoylamino)-4-aminobenzene-2,5-disulphonic acid, 1,4-diaminobenzene-2-carboxylic acid, 1,3-diaminobenzene-4-carboxylic acid, 1,2-diaminobenzene-4-carboxylic acid, 1,3-diaminobenzene-5-carboxylic acid, 1,4-diaminobenzene-2-methylbenzene, 4,4'-diaminodiphenyl oxide, 4,4'-diaminodiphenylurea-2,2'-disulphonic acid, 4,4'-diaminodiphenyloxyethane-2,2'-disulphonic acid, 4,4'-diaminostilbene-2,2'-disulphonic acid, 4,4'-diaminodiphenylethane-2,2'-disulphonic acid, 2-amino-5-aminomethylnaphthalene-1-sulphonic acid, 2-amino-5-aminomethylnaphthalene-1,7-disulphonic acid, 1-amino-4-methoxy-5-aminomethylbenzene-6-sulphonic acid, 1-amino-3-(N-methyl)-aminomethylbenzene-6-sulphonic acid, 1-amino-4-(N-methyl)-aminomethylbenzene-3-sulphonic acid, 1-amino-4-aminomethylbenzene-3-sulphonic acid, 1,3-diaminobenzene-4-(azophenyl-4'-sulphonic acid), 1,3-diaminobenzene-4-(azophenyl-2',4'-disulphonic acid), 1,3-diaminobenzene-6-sulphonic acid-4-(azophenyl-4'-sulphonic acid), 1,3-diaminobenzene-6-sulphonic acid-4-(azophenyl-3',6'-disulphonic acid).

If an aminoacetyl compound from which the acetyl group is subsequently split off again by hydrolysis, as is described above in the explanations of the process variants, is to be employed instead of a diamine as the diazo component, the monoacetyl compounds of the above-mentioned diazo components are possible, for example 1-acetylamino-3-aminobenzene-4-sulphonic acid or 1-acetylamino-4-aminobenzene-3-sulphonic acid.

Coupling Components (H—[KK]—$NR^0H$)

1-Amino-8-hydroxynaphthalene-6-sulphonic acid, 1-amino-8-hydroxynaphthalene-2,4-disulphonic acid, 2-hydroxy-3-aminonaphthalene-5,7-disulphonic acid, 1-amino-8-hydroxynaphthalene-2,4,6-trisulphonic acid, 1-hydroxy-8-acetyl-aminonaphthalene-3-sulphonic acid, 2-amino-5-hydroxynaphthalene-7-sulphonic acid, 2-methyl- or 2-ethylamino-5-hydroxynaphthalene-7-sulphonic acid, 2-(N-acetyl-N-methylamino)-5-hydroxynaphthalene-7-sulphonic acid, 2-acetylamino-5-hydroxynaphthalene-7-sulphonic acid, 2-amino-5-hydroxynaphthalene-1,7-disulphonic acid, 2-amino-8-hydroxynaphthalene-6-sulphonic acid, 2-(N-acetyl-N-methylamino)-8-hydroxynaphthalene-6-sulphonic acid, 2-acetylamino-8-hydroxynaphthalene-6-sulphonic acid, 2-amino-8-hydroxynaphthalene-3,6-disulphonic acid, 2-acetylamino-8-hydroxynaphthalene-3,6-disulphonic acid, 1-amino-5-hydroxynaphthalene-7-sulphonic acid, 1-amino-8-hydroxynaphthalene-3,6- or -4,6-disulphonic acid, 1-acetylamino-8-hydroxynaphthalene-3,6- or -4,6-disulphonic acid, 1-(4'-aminobenzoylamino)-8-hydroxynaphthalene-3,6- or -4,6-disulphonic acid, 1-(4'-nitrobenzoylamino)-8-hydroxynaphthalene-3,6- or -4,6-disulphonic acid, 1-(3'-aminobenzoylamino)-8-hydroxynaphthalene-3,6- or -4,6-disulphonic acid, 1-(3'-nitrobenzoylamino)-8-hydroxynaphthalene-3,6- or -4,6-disulphonic acid, 1-amino-8-hydroxynaphthalene-4-sulphonic acid.

The diazotization of the diazo components or of the intermediate products containing a diazotizable amino group is as a rule carried out by the action of nitrous acid in aqueous-mineral acid solution at a low temperature. The coupling to the coupling components is carried out at weakly acid, neutral to weakly alkaline pH values.

The condensation of the reactive components with the diazo components and the coupling components and with the amines or with acylatable monoazo or diazo intermediate products or with the dyestuffs containing amino groups is preferably carried out in aqueous solution or suspension at a low temperature and at a weakly acid, neutral to weakly alkaline pH value. Preferably, the hydrogen halide liberated during the condensation is neutralized continuously by addition of aqueous alkali metal hydroxides, bicarbonates or carbonates.

The formulae shown are those of the free acids. In general, the salts, in particular the alkali metal salts, such as sodium, potassium or lithium salts, are obtained in the preparation. The charge formed by quaternization with pyridines is compensated by a counterion, for example chloride, fluorine or sulphate, depending on the isolation conditions; or the dyestuffs form inert salts with sulpho or carboxyl groups. The dyestuffs can also be employed as concentrated solutions.

The reactive dyestuffs of the formula (I) are suitable for dyeing and printing naturally occurring or synthetic materials containing hydroxyl groups or amide groups, such as silk, leather, wool and synthetic polyamide fibres, but in particular cellulose-containing materials having a fibrous structure, such as linen, cellulose, regenerated cellulose and above all cotton. They are suitable both for the exhaust process and for dyeing by the customary pad-dyeing processes, in which the goods are impregnated with aqueous and if appropriate also salt-containing dyestuff solutions and the dyestuffs are fixed after treatment with alkali or in the presence of alkali, if appropriate under the action of heat.

The reactive dyestuffs of the formula (I) are distinguished by a high reactivity and excellent fixing capacity. Because of their trifunctionality, they also give high fixing yields from a long liquor. They are characterized by the yield being relatively independent of the dyeing temperature, and can therefore be employed in the exhaust process at low to moderate dyeing temperatures. In the pad-steam process, they require only short steaming times. They produce dyeings of good colour strength with good light- and wet-fastnesses.

The invention furthermore relates to textile products comprising materials containing hydroxyl groups or amide groups which have been dyed with dyestuffs of the formula (I).

The $\lambda_{max}$ values of the dyestuffs from the following examples were measured in water, unless stated otherwise.

EXAMPLE 1

A) 0.1 mol of 1-amino-8-hydroxy-3,6-naphthalene-disulphonic acid (H acid) was suspended in 150 parts of ice and 150 parts of water and dissolved with lithium hydroxide solution at pH 6. 0.11 mol of 2,4,6-trichloro-1,3,5-triazine was added, and the pH was allowed to fall to 4 and was kept at this level with lithium carbonate until the condensation had ended.

B) The above solution was added dropwise at pH 8 and 20° C. to a solution of 0.11 mol of the compound of the formula

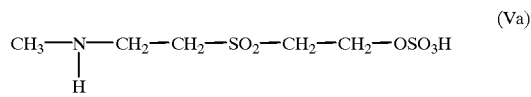

in 50 parts of water in the course of 10 minutes, during which the pH was kept constant with lithium hydroxide solution.

C) 0.1 mol of 2-amino-1-naphthalenesulphonic acid was diazotized in the customary manner and coupled at pH 7.5–8.5 to the H acid condensation product. The dyestuff was salted out by addition of potassium chloride and isolated. Drying gave about 35 g of a salt-containing dyestuff powder. This dyestuff has the following structure

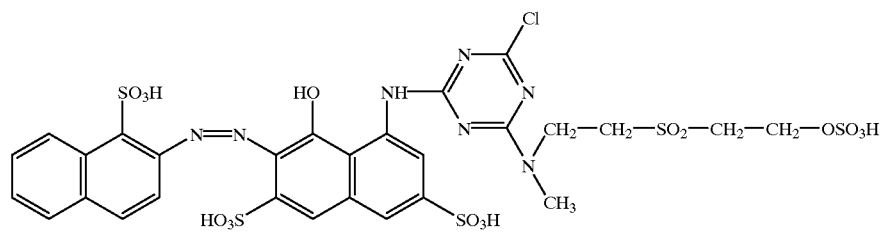

and dyes cotton in red colour shades by the dyeing or printing processes customary for reactive dyestuffs. $\lambda_{max}$= 522 nm, 545 nm (water)

EXAMPLE 2

A) 0.1 mol of 1-amino-5-hydroxy-2-naphthalene-sulphonic acid (I acid) was suspended in 300 parts of ice and 300 parts of water and dissolved with lithium hydroxide solution at pH 6. 0.15 mol of 2,4,6-tri-fluoro-1,3,5-triazine was added dropwise at pH 4.5 in the course of 10 minutes, during which the pH was kept constant with lithium carbonate.

B) The above suspension was added dropwise at pH 8 and 20° C. to a solution of 0.12 mol of the compound of the formula Va in 50 parts of water in the course of 10 minutes, during which the pH was kept constant with lithium hydroxide solution.

C) 0.1 mol of 2-amino-1,5-naphthalenedisulphonic acid was suspended in 200 parts of water and 100 parts of ice at 0° C. 28 parts of concentrated hydrochloric acid were added. A solution of 7 parts of sodium nitrite in 70 parts of water was added dropwise in the course of 15 minutes. After subsequent stirring for 30 minutes, the diazotization had ended. A pale yellow suspension resulted. The excess nitrite was destroyed with amidosulphonic acid.

This suspension was then metered in to 0.1 mol of the I acid condensation product over a period of 15–20 minutes. Coupling was carried out at 20° C. and a pH of 7–8. The dyestuff was precipitated by addition of ethanol and isolated. Drying gave about 40 g of a dyestuff powder. The structure of the dyestuff corresponds to the formula

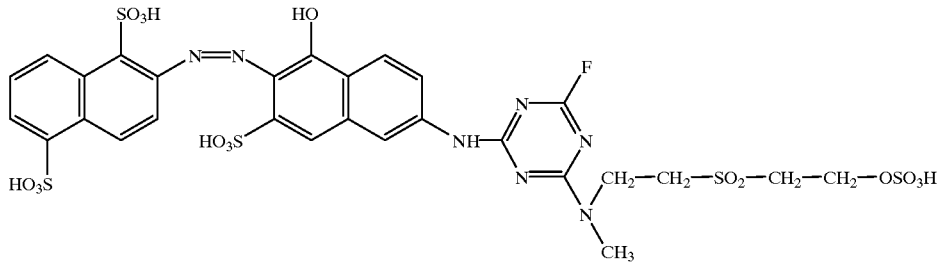

and the dyestuff dyes cotton orange by the dyeing and printing processes customary for reactive dyestuffs. $\lambda_{max}$= 484 nm Other reactive dyestuffs were obtained by condensation of the following components:

| No. | Diazo component | 1-Amino-8-hydroxy-napphthalene-disulphonic acid | Trihalogeno-triazine | Component of formula (V) | Colour shade | $\lambda_{max}$ (nm) |
|---|---|---|---|---|---|---|
| 3 | 2-aminobenzenesulphonic acid (SO₃H, NH₂ on benzene) | 1-amino-8-hydroxy-naphthalene-3,6-disulphonic acid structure | 2,4,6-trifluoropyrimidine | HN—CH₂—CH₂—SO₂—CH₂—CH₂—OSO₃H with CH₃ branch | red | 513, 531 |
| 4 | 2-aminobenzenesulphonic acid | 1-amino-8-hydroxy-naphthalene disulphonic acid | 2,4,6-trifluoropyrimidine | " | red | |
| 5 | 2-amino-1-naphthalenesulphonic acid | 1-amino-8-hydroxy-naphthalene disulphonic acid | 2,4,6-trifluoropyrimidine | " | bluish-tinged red | |
| 6 | 2-amino-1,5-naphthalenedisulphonic acid | 1-amino-8-hydroxy-naphthalene disulphonic acid | 2,4,6-trifluoropyrimidine | " | red | |

-continued

| No. | Diazo component | 1-Amino-8-hydroxy-napphthalene-disulphonic acid | Trihalogeno-triazine | Component of formula (V) | Colour shade | $\lambda_{max}$ (nm) |
|---|---|---|---|---|---|---|
| 7 | 2-amino-5-chloro-benzenesulphonic acid structure | H-acid (NH₂/OH with 2 SO₃H) | 2,4,6-trifluoropyrimidine | HN—CH₂—CH₂—SO₂—CH₂—CH₂—CH₂—OSO₃H<br>│<br>CH₃ | red | |
| 8 | 2-amino-5-methyl-benzenesulphonic acid | H-acid | 2,4,6-trifluoropyrimidine | " | red | 518 |
| 9 | 2-amino-1-naphthalenesulphonic acid | K-acid isomer (NH₂/OH naphthalene disulphonic) | 2,4,6-trichlorotriazine | " | bluish-tinged red | |
| 10 | 2-amino-1,5-naphthalenedisulphonic acid | K-acid isomer | 2,4,6-trichlorotriazine | " | red | |

| No. | Diazo component | 1-Amino-8-hydroxy-naphthalene-disulphonic acid | Trihalogeno-triazine | Component of formula (V) | Colour shade | $\lambda_{max}$ (nm) |
|---|---|---|---|---|---|---|
| 11 | H₃CO-C₆H₃(SO₃H)(NH₂) | 2-amino-5-hydroxy-7-sulfo-naphthalene (OH, NH₂, SO₃H) | 2,4,6-trifluoro-triazine | HN—CH₂—CH₂—SO₂—CH₂—CH₂—OSO₃H, with CH₃ branch | yellowish-tinged | 501 |
| 12 | H₃C-C₆H₃(SO₃H)(NH₂) | same naphthalene | 2,4,6-trichloro-triazine | " | orange | |
| 13 | 1-sulfo-2-amino-naphthalene | same naphthalene | 2,4,6-trichloro-triazine | " | red | |
| 14 | 1,5-disulfo-2-amino-naphthalene | 4,8-diamino-1-hydroxy-naphthalene-3,6-disulfonic type (NH₂, SO₃H, OH, HO₃S) | 2,4,6-trichloro-triazine | " | red | 518, 541 |

-continued

| No. | Diazo component | 1-Amino-8-hydroxy-napththalene-disulphonic acid | Trihalogeno-triazine | Component of formula (V) | Colour shade | $\lambda_{max}$ (nm) |
|---|---|---|---|---|---|---|
| 15 | 2-amino-5-methylbenzenesulphonic acid (H₃C–, SO₃H, NH₂) | 7-amino-1-hydroxynaphthalene-3-sulphonic acid (NH₂, OH, HO₃S) | 2,4,6-trichloro-1,3,5-triazine (Cl, Cl, Cl) | HN—CH₂—CH₂—SO₂—CH₂—CH₂—OSO₃H, with CH₃ branch | orange | |
| 16 | 2-amino-4-acetamidobenzenesulphonic acid (SO₃H, NH₂, NH–COCH₃) | 8-amino-1-hydroxynaphthalene-3,6-disulphonic acid (NH₂, SO₃H, OH, HO₃S) | 2,4,6-trifluoro-1,3,5-triazine (F, F, F) | " | red | |
| 17 | 4-aminobenzenesulphonic acid (NH₂, HO₃S) | 8-amino-1-hydroxynaphthalene-3,6-disulphonic acid (NH₂, SO₃H, OH, HO₃S) | 2,4,6-trifluoro-1,3,5-triazine (F, F, F) | " | red | |
| 18 | 2-aminobenzenesulphonic acid (NH₂, SO₃H) | 8-(4-aminobenzamido)-1-hydroxynaphthalene-3,6-disulphonic acid (NH₂, NH–CO, SO₃H, OH, HO₃S) | 2,4,6-trifluoro-1,3,5-triazine (F, F, F) | " | red | |

EXAMPLE 19

0.1 mol of the monoazo compound having the formula

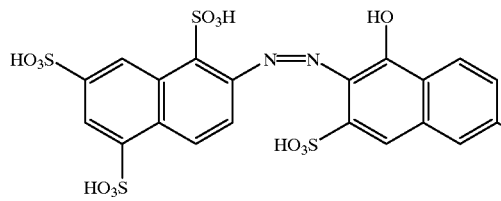

was dissolved in 500 parts of water and 200 parts of ice with lithium hydroxide solution at pH 6. 0.15 mol of 2,4,6-trifluoro-1,3,5-triazine was added dropwise at pH 4.5 in the course of 10 minutes, during which the pH was kept constant with lithium carbonate.

The above solution was added dropwise at pH 8 and 20° C. to a solution of 0.12 mol of the compound of the formula (Va) in 50 parts of water in the course of 10 minutes, during which the pH was kept constant with lithium hydroxide solution.

The dyestuff was salted out by addition of potassium chloride, isolated and dried. About 72 g of a salt-containing dyestuff which has the structure

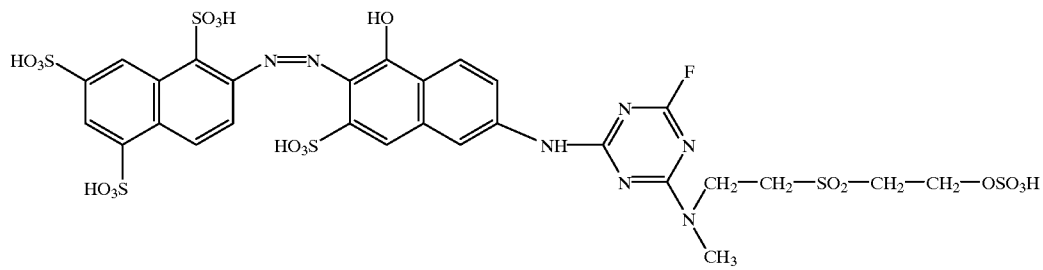

and which dyes cotton in orange colour shades by the dyeing and printing processses customary for reactive dyestuffs were obtained. $\lambda_{max}$=483 nm Other reactive dyestuffs were obtained by condensation of trifluorotriazine and the following components analogously to Example 19.

| No. | Aminoazo dyestuff | Component of the Formula (V) | colour shade | $\lambda_{max}$ |
|---|---|---|---|---|
| 20 | (naphthalene-azo-naphthalene structure with OH, NH$_2$, SO$_3$H groups) | HN—CH$_2$—CH$_2$—SO$_2$—CH$_2$—CH$_2$OSO$_3$H<br>\|<br>CH$_3$ | orange | |
| 21 | (naphthalene-azo-naphthalene structure with OH, NH$_2$, SO$_3$H groups) | " | orange | |
| 22 | (naphthalene-azo-naphthalene structure with OH, NHCH$_3$, SO$_3$H groups) | " | orange | |
| 23 | (phenyl-azo-naphthalene structure with OH, NH$_2$, SO$_3$H, OCH$_3$ groups) | HNCH$_2$CH$_2$—SO$_2$—CH$_2$—CH$_2$OSO$_3$H<br>\|<br>CH$_3$ | orange | 497 |

-continued

| No. | Aminoazo dyestuff | Component of the Formula (V) | colour shade | $\lambda_{max}$ |
|---|---|---|---|---|
| 24 | (structure) | " | orange | 488 |
| 25 | (structure) | " | orange | 489 |
| 26 | (structure) | HNCH$_2$CH$_2$—SO$_2$CH$_2$CH$_2$OSO$_3$H<br>—CH$_3$ | yellowish-tinged red | 512 |
| 27 | (structure) | " | yellowish-tinged red | |

-continued

| No. | Aminoazo dyestuff | Component of the Formula (V) | colour shade | $\lambda_{max}$ |
|---|---|---|---|---|
| 28 | (structure: naphthalene with OH, two NH₂, SO₃H, N=N-phenyl with SO₃H and OCH₃/H₃CO) | " | yellowish-tinged red | 513 |
| 29 | (structure: naphthalene with OH, NH₂, SO₃H, N=N-naphthyl with SO₃H) | $HNCH_2CH_2-SO_2-CH_2-CH_2OSO_3H$<br>$\quad\mid$<br>$\quad CH_3$ | orange | |
| 30 | (structure: naphthalene with OH, NH₂, SO₃H, N=N-naphthyl with SO₃H, SO₃H) | " | scarlet | |
| 31 | (structure: naphthalene with OH, NH₂, SO₃H, N=N-naphthyl with SO₃H, SO₃H, HO₃S) | " | scarlet | |

EXAMPLE 32

0.1 mol of the monoazo dyestuff of the formula

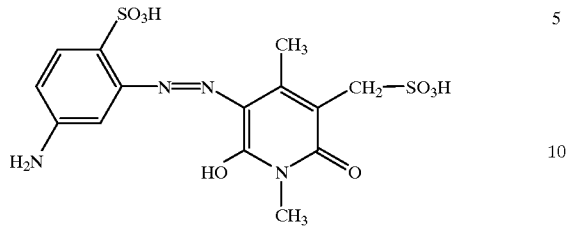

was reacted with 2,4,6-trifluoro-1,3,5-triazine and the compound of the formula (Va) analogously to Example 19

About 105 g of a salt-containing dyestuff which has the structure

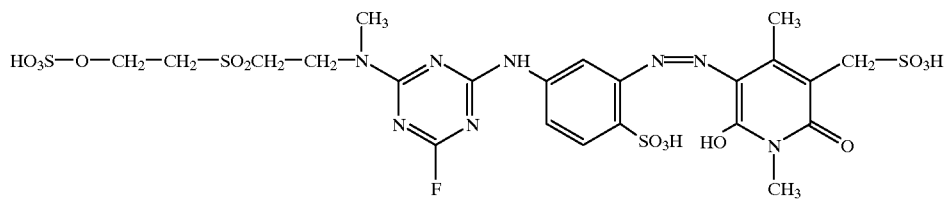

and dyes cotton in yellow colour shades by the dyeing or printing processes customary for reactive dyestuffs were obtained. $\lambda_{max}$=421 nm Other yellow reactive dyestuffs were obtained by condensation of the following components:

| No. | Axo component | Trihalogenotriazine | Component of the formula (V) | Colour shade | $\lambda_{max}$ (nm) |
|---|---|---|---|---|---|
| 33 | | | HN—CH$_2$—CH$_2$—SO$_2$—CH$_2$—CH$_2$—OSO$_3$H<br>|<br>CH$_3$ | greenish-tinged yellow | |
| 34 | | | " | greenish-tinged yellow | |
| 35 | | | " | yellow | |
| 36 | | | " | yellow | |

| No. | Azo component | Trihalogenotriazine | Component of the formula (V) | Colour shade | $\lambda_{max}$ (nm) |
|---|---|---|---|---|---|
| 37 | | 2,4,6-trifluoropyrimidine | HN—CH$_2$—CH$_2$—SO$_2$—CH$_2$—CH$_2$OSO$_3$H<br>  \|<br>  CH$_3$ | greenish-tinged yellow | |
| 38 | | 2,4,6-trifluoropyrimidine | " | greenish-tinged yellow | 422 |
| 39 | | 2,4,6-trichloropyrimidine | " | greenish-tinge yellow | |
| 40 | | 2,4,6-trichloropyrimidine | " | greenish-tinged yellow | 421 |

-continued

| No. | Azo component | Trihalogenotriazine | Component of the formula (V) | Colour shade | $\lambda_{max}$ (nm) |
|---|---|---|---|---|---|
| 41 | (structure with SO₃H, CH₃, CONH₂, N=N, pyridone with CH₃, OH, CH₂NHCH₃) | 2,4,6-trifluorotriazine | HNCH₂CH₂SO₂CH₂CH₂OSO₃H with CH₃ | greenish-tinged yellow | |
| 42 | (structure with SO₃H, CH₂, CH₃·SO₃H, N=N, pyridone with CH₂, OH, CH₂NHCH₂) | " | " | greenish-tinged yellow | |
| 43 | (structure with SO₃H, N=N, H₂N, pyridone with CH₃, CH₃·SO₃H, OH, C₂H₅) | 2,4,6-trichlorotriazine | " | greenish-tinged yellow | 421 |
| 44 | (naphthalene with SO₃H, SO₃H, N=N, pyridone with CH₃, CONH₂, OH, CH₂—CH₂NH₂) | " | " | yellow | |

EXAMPLE 45

0.1 mol of the monoazo dyestuff of the formula

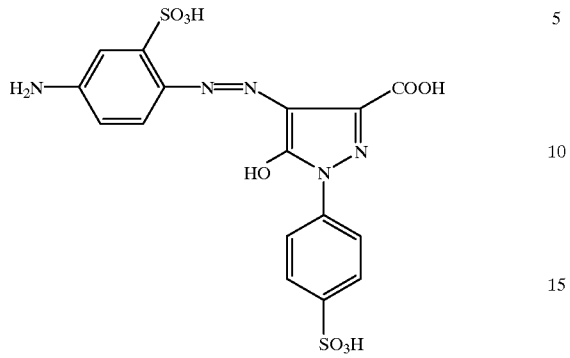

was reacted with 2,4,6-trifluoro-1,3,5-triazine and the compound of the formula (Va) analogously to Example 19.

About 105 g of a salt-containing dyestuff powder which has the structure

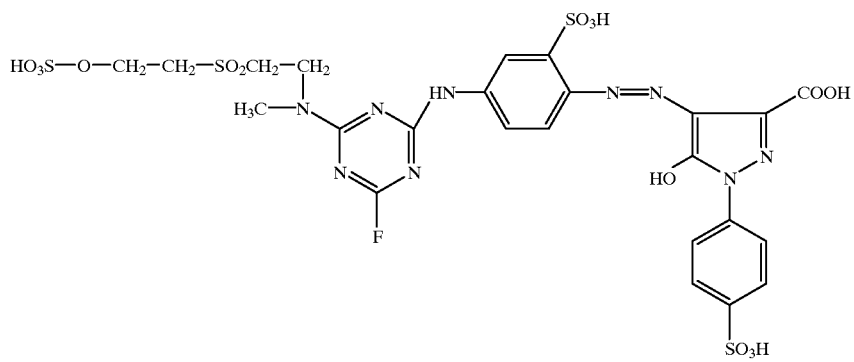

and dyes cotton in yellow colour shades by the dyeing or printing processes customary for reactive dyestuffs were obtained.

Other yellow dyestuffs having similar properties were obtained when the following aminophenylazopyrazolones were subjected to condensation with cyanuric fluoride and the compound of the formula (V) shown.

| No. | Aminophenylaxopyrazolone | Component of the formula (V) |
|---|---|---|
| 46 | ![] H$_2$N-C$_6$H$_3$(SO$_3$H)-N=N-pyrazole(COOH)(N-C$_6$H$_4$-SO$_3$H) | HN—CH$_2$—CH$_2$—SO$_2$—CH$_2$OSO$_3$H<br>\|<br>CH$_3$ |

-continued

| No. | Aminophenylaxopyrazolone | Component of the formula (V) |
|---|---|---|
| 47 | 4-amino-2-sulfo-phenyl azo coupled to 1-(2-methyl-4-sulfophenyl)-3-carboxy-5-hydroxypyrazole | |
| 48 | 5-amino-2-sulfo-phenyl azo coupled to 1-(2,5-dichloro-4-sulfophenyl)-3-carboxy-5-hydroxypyrazole | |
| 49 | 5-amino-2-sulfo-phenyl azo coupled to 1-(4,8-disulfonaphth-2-yl)-3-methyl-5-hydroxypyrazole | $HN-CH_2-CH_2-SO_2-CH_2OSO_3H$ with $CH_3$ on N |
| 50 | 5-amino-2-sulfo-phenyl azo coupled to 3-methyl-5-hydroxy-1H-pyrazole | |
| 51 | 5-amino-2-sulfo-phenyl azo coupled to 1-(2-chloro-5-sulfophenyl)-3-methyl-5-hydroxypyrazole | |

-continued

| No. | Aminophenylaxopyrazolone | Component of the formula (V) |
|---|---|---|
| 52 | 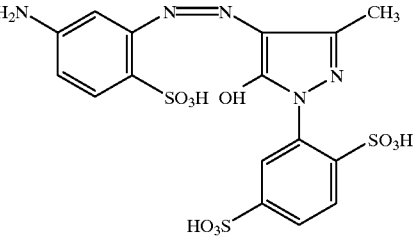 | |

EXAMPLE 53

0.1 mol of the monoazo dyestuff of the formula

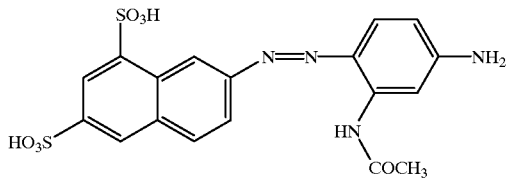

was reacted with 2,4,6-trifluoro-1,3,5-triazine and the compound of the formula (Va) analogously to Example 19.

1.5 g of phosphate buffer of pH 6 were added to the resulting solution and the mixture was evaporated in vacuo at 35 to 40° C. or spray dried.

The resulting dyestuff of the formula

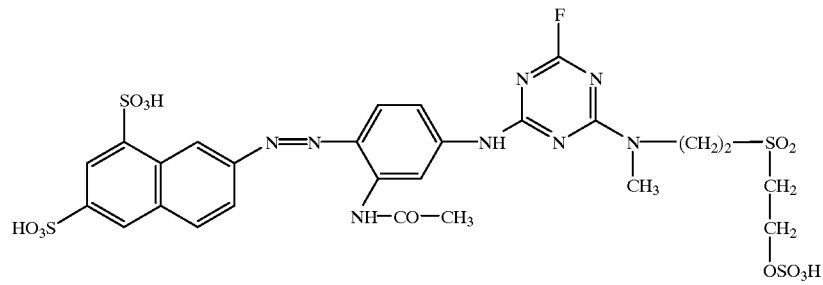

dyes cotton in golden yellow shades from a long liquor. $\lambda_{max}$=389 nm

Other dyestuffs which give reddish-tinged yellow dyeings were obtained by condensation of the following p-aminoazo compounds with cyanuric fluoride or cyanuric chloride and compounds of the formula (V).

| No. | Aminoazo dyestuff | Trihalogenotriazine | Component of the formula (V) | Colour shade | $\lambda_{max}$ (nm) |
|---|---|---|---|---|---|
| 54 | (naphthalene with SO₃H, HO₃S, SO₃H)–N=N–(benzene with NH₂, NH–CO–NH₂) | 2,4,6-trifluorotriazine | HNCH₂CH₂–SO₂–CH₂–CH₂OSO₃H with CH₃ | reddish-tinged yellow | 419 |
| 55 | (naphthalene with SO₃H, HO₃S)–N=N–(benzene with NH₂, NH–CONH₂) | 2,4,6-trifluorotriazine | " | reddish-tinged yellow | 399 |
| 56 | (naphthalene with SO₃H, SO₃H)–N=N–(benzene with NH₂, NH–CONH₂) | 2,4,6-trifluorotriazine | " | reddish-tinged yellow | 389 |
| 57 | (naphthalene with SO₃H, SO₃H)–N=N–(benzene with NH₂, NH–CO–NH₂) | 2,4,6-trifluorotriazine | " | reddish-tinged yellow | 395 |
| 58 | (naphthalene with SO₃H, HO₃S, SO₃H)–N=N–(benzene with NH₂, NH–COCH₂) | 2,4,6-trifluorotriazine | HNCH₂CH₂–SO₂–CH₂–CH₂OSO₃H with CH₃ | reddish-tinged yellow | 401 |

-continued

| No. | Aminoazo dyestuff | Trihalogenotriazine | Component of the formula (V) | Colour shade | $\lambda_{max}$ (nm) |
|---|---|---|---|---|---|
| 59 | | 2,4,6-trifluorotriazine | " | reddish-tinged yellow | |
| 60 | | 2,4,6-trifluorotriazine | " | reddish-tinged yellow | |
| 61 | | 2,4,6-trifluorotriazine | " | reddish-tinged yellow | |
| 62 | | 2,4,6-trichlorotriazine | $HNCH_2CH_2-SO_2-CH_2-CH_2OSO_3H$ <br> $\quad\quad\quad CH_3$ | reddish-tinged yellow | 401 |
| 63 | | 2,4,6-trifluorotriazine | " | reddish-tinged yellow | |

-continued

| No. | Aminoazo dyestuff | Trihalogenotriazine | Component of the formula (V) | Colour shade | $\lambda_{max}$ (nm) |
|---|---|---|---|---|---|
| 64 | (structure) | trifluorotriazine | " | orange | |
| 65 | (structure) | trichlorotriazine | HNCH$_2$CH$_2$—SO$_2$—CH$_2$CH$_2$OSO$_3$H<br>       \|<br>      CH$_3$ | reddish-tinged yellow | 402 |
| 66 | (structure) | trichlorotriazine | " | reddish-tinged yellow | |
| 67 | (structure) | trichlorotriazine | " | reddish-tinged yellow | |
| 68 | (structure) | trichlorotriazine | " | reddish-tinged yellow | |

EXAMPLE 69

0.1 mol of the monoazo dyestuff of the formula

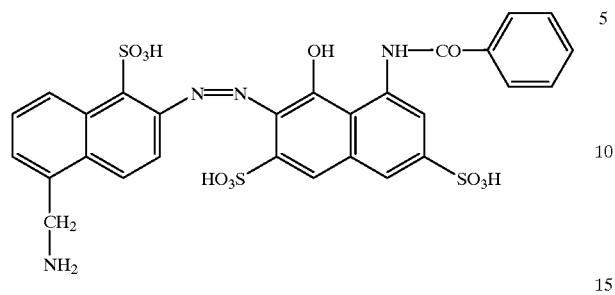

was reacted with 2,4,6-trifluoro-1,3,5-triazine and the compound of the formula (Va) analogously to Example 19. When the condensation had ended, the dyestuff was isolated by salting out and filtration with suction and, after buffering to a pH of 6.5, was dried in vacuo at 45° C. It corresponds to the formula

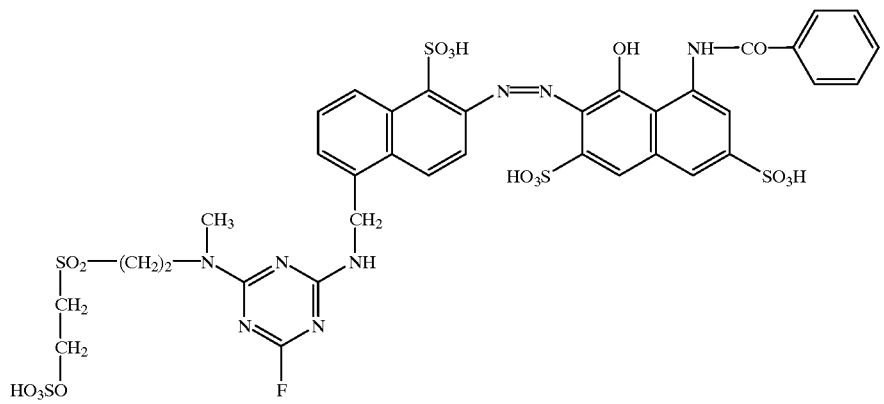

and dyes cotton in bluish-tinged red shades with a good fixing yield from a long liquor. $\lambda_{max}$=520 nm, 544 nm Similar red dyestuffs were obtained by reaction of the following components:

| No. | Diaminobenzene-sulphonic acid | Trihalogenotriazine | Coupling component | Component of the formula (V) | Colour shade | $\lambda_{max}$ (nm) |
|---|---|---|---|---|---|---|
| 70 | 2,4-diaminobenzenesulphonic acid (NH₂, NH₂, SO₃H) | trifluorotriazine | 8-benzamido-1-hydroxy-3,6-disulphonic acid naphthalene | HNCH₂CH₂—SO₂—CH₂—CH₂OSO₃H, CH₃ | red | 514 |
| 71 | 2,4-diaminobenzenesulphonic acid | trifluorotriazine | 8-benzamido-1-hydroxy-3,6-disulphonic acid naphthalene | " | blusish-tinged red | |
| 72 | 2,4-diaminobenzenesulphonic acid | trifluorotriazine | 8-acetamido-1-hydroxy-3,6-disulphonic acid naphthalene | " | red | |
| 73 | 2,4-diamino-3-methyl-5-sulphonic acid benzene | trifluorotriazine | 8-propionamido-1-hydroxy-3,6-disulphonic acid naphthalene | " | red | |

| No. | Azo component | Trihalogenotriazine | Component of formula (V) | Colour shade | $\lambda_{max}$ (nm) |
|---|---|---|---|---|---|
| 74 | | | HNCH$_2$CH$_2$—SO$_2$—CH$_2$—CH$_2$—OSO$_3$H<br>  \|<br>  CH$_3$ | red | |
| 75 | | | " | bluish-tinged red | |
| 76 | | | " | red | |
| 77 | | | " | yellowish-tinged red | |

| No. | Diaminobenzene-sulphonic acid | Trihalogenotriazine | Coupling component | Component of the formula (V) | Colour shade | $\lambda_{max}$ (nm) |
|---|---|---|---|---|---|---|
| 80 | | | | HNCH$_2$CH$_2$—SO$_2$—CH$_2$—CH$_2$OSO$_3$H<br>        |<br>     CH$_3$ | bluish-tinged red | |
| 81 | | | | " | red | 515 |
| 82 | | | | " | red | 515, 536 |

Where * identifies the atom bonded to the triazine ring.

EXAMPLE 83

36.7 g of the amino-disazo compound, prepared by the known route, of the formula

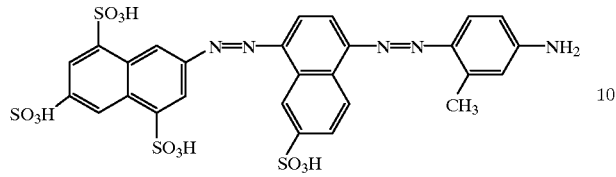

were reacted with 2,4,6-trifluoro-1,3,5-triazine and the compound of the formula (Va) analogously to Example 19.

The resulting dyestuff of the formula

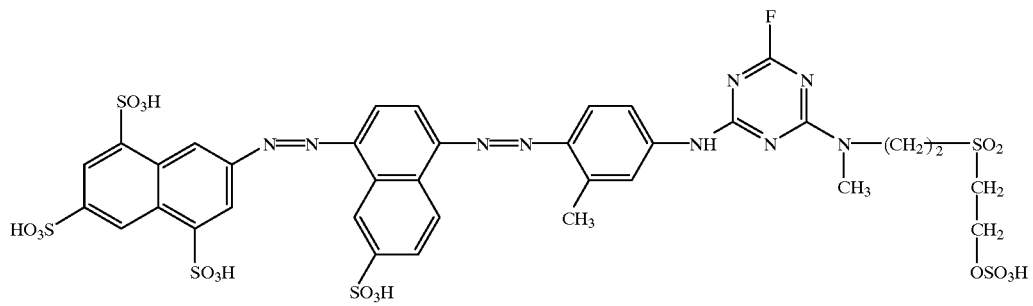

was salted out with sodium chloride, filtered off with suction and, after buffering at pH 6, dried in vacuo at 45° C. It dyes cotton in brown shades with a high yield by the processes known for reactive dyestuffs. $\lambda_{max}$=463 nm

EXAMPLE 83a

If, instead of the aminodisazo compound of Example 83, the compound of the formula

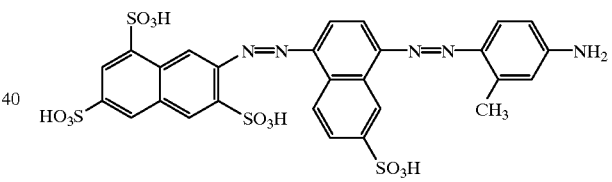

was employed, a dyestuff of the formula

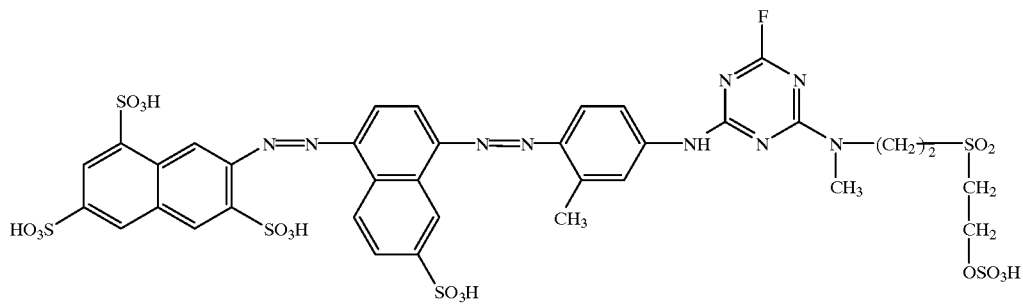

which likewise dyes cotton in brown shades with a high yield was obtained.

Other brown reactive dyestuffs were obtained by condensation of the following components:

| No. | Aminodisazo compound | Trihalogenotriazine | Component of the formula (V) | Colour shade |
|---|---|---|---|---|
| 84 | | trifluorotriazine | HNCH$_2$CH$_2$—SO$_2$—CH$_2$—CH$_2$OSO$_3$H<br>    \|<br>   CH$_3$ | brown |
| 85 | | trifluorotriazine | " | brown |
| 86 | | trifluorotriazine | " | brown |
| 87 | | trifluorotriazine | " | orange-brown |

EXAMPLE 88

50.3 g of aminoazo compound (0.1 mol) of the formula

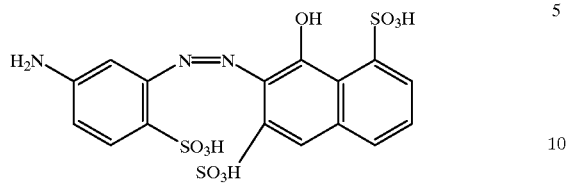

were reacted with 2,4,6-trifluoro-1,3,5-triazine and the compound of the formula (Va) analogously to Example 19. Thereafter, the dyestuff of the formula

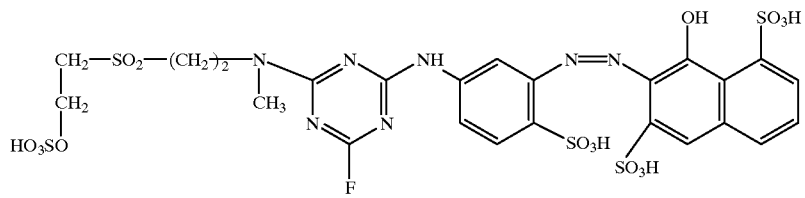

was isolated by salting out and filtration with suction. After gentle drying, a powder which dyes cotton in scarlet shades with a high yield by the customary methods was obtained.

Other reactive dyestuffs based on aminoazonaphthol compounds were obtained by condensation of the following components.

| No. | Aminoazonaphthol component | Trihalogenotriazine | Component of the formula (V) | Colour shade |
|---|---|---|---|---|
| 89 | | | $HNCH_2CH_2$—$SO_2$—$CH_2$—$CH_2OSO_3H$ with $CH_3$ on N | orange |
| 90 | | | " | orange |
| 91 | | | " | yellowish-tinged red |
| 92 | | | " | " |

EXAMPLE 93

0.1 mol of the known compound

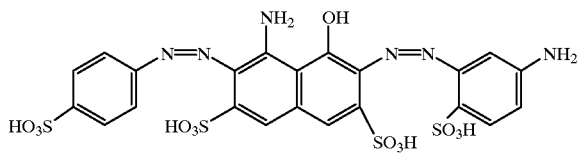

was reacted with 2,4,6-trifluoro-1,3,5-triazine and the compound of the formula (Va) analogously to Example 19.

When the condensation had ended, the dyestuff was isolated, after buffering to pH 6, either directly by spray drying or by salting out, filtration with suction and vacuum drying at 40° C. The dyestuff has the formula

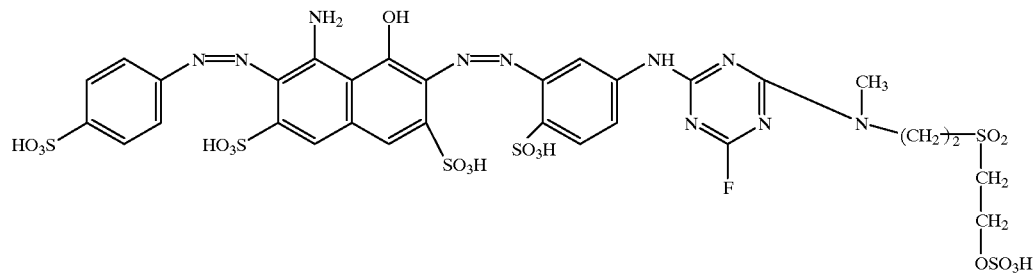

and dyes cotton in navy blue shades with a very good yield by the dyeing techniques customary for reactive dyestuffs.

Other similar reactive dyestuffs which dye cellulose fibres navy blue to black were obtained when the aminodisazo components of the general formula

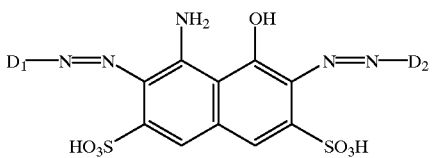

shown in the following list were subjected to condensation with the trihalogenotriazines and compounds of the formula (V).

| No. | Aminodisazo compound | | | Colour | |
|---|---|---|---|---|---|
| | $D_1$ | $D_2$ | Trihalogenotriazine | Component of the formula (V) | shade |
| 94 | 4-methylphenyl-SO$_3$H | 3-methyl-4-SO$_3$H-aniline (NH$_2$) | 2,4,6-trifluorotriazine | HN—CH$_2$—CH$_2$—SO$_2$—CH$_2$—CH$_2$—CH$_2$—OSO$_3$H<br>        │<br>        CH$_3$ | navy |
| 95 | 4-H$_2$N-O$_2$S-phenyl | 3-methyl-4-SO$_3$H-aniline | 2,4,6-trifluorotriazine | " | navy |
| 96 | 2-methyl-4-SO$_3$H-phenyl-SO$_3$H | 3-methyl-4-SO$_3$H-aniline | 2,4,6-trifluorotriazine | " | navy |
| 97 | 2-methyl-4-NH$_2$-phenyl-SO$_3$H | 3-methyl-benzene-SO$_3$H | 2,4,6-trifluorotriazine | " | navy |

-continued

| | Aminodisazo compound | | | Colour | |
|---|---|---|---|---|---|
| No. | D$_1$ | D$_2$ | Trihalogenotriazine | Component of the formula (V) | shade |
| 98 | 4-HO$_3$S-C$_6$H$_4$- | 2-NH$_2$-4-SO$_3$H-5-CH$_3$-C$_6$H$_2$-SO$_3$H | 2,4,6-trifluoropyrimidine | HNCH$_2$CH$_2$—SO$_2$—CH$_2$—CH$_2$OSO$_3$H<br>                                                                                CH$_3$ | black |
| 99 | 2-CH$_3$-5-SO$_3$H-C$_6$H$_3$- | 4-NH$_2$-3-CH$_3$-C$_6$H$_3$-SO$_3$H | 2,4,6-trichlorotriazine | " | navy |
| 100 | 2-CH$_3$-1,5-di-SO$_3$H-naphthyl- | 4-NH$_2$-3-CH$_3$-C$_6$H$_3$-SO$_3$H | 2,4,6-trifluoropyrimidine | " | black |

EXAMPLE 101

0.1 mol of the copper complex compound of the formula

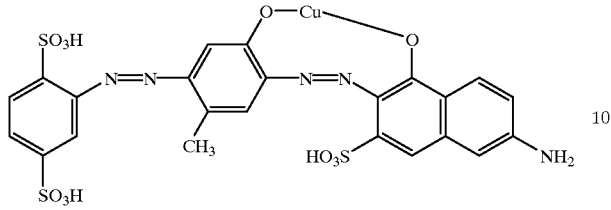

was reacted with 2,4,6-trifluoro-1,3,5-triazine and the compound of the formula (Va) analogously to Example 19.

When the reaction had ended, the dyestuff of the formula

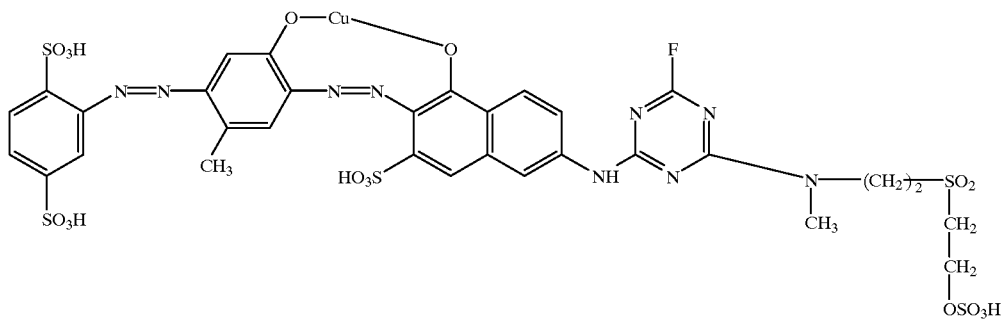

was salted out, isolated and, after buffering to pH 6, dried in vacuo at 45° C.

The product dyes cellulose fibres in navy blue shades with a very good fixing yield by the dyeing techniques customary for reactive dyestuffs.

Other reactive dyestuffs which dye cotton with a very good yield by the customary dyeing techniques were obtained when the known copper complex compounds shown in the following list were subjected to condensation with the trihalogenotriazines and the components of the formula (V) by the procedures described in Example 101.

| No. | Copper complex compound | Trihalogenotriazine | Component of the formula (V) | Colour shade | $\lambda_{max}$ (nm) |
|---|---|---|---|---|---|
| 102 | | | HN—(CH$_2$)$_2$—SO$_2$—CH$_2$—CH$_2$OSO$_3$H<br>       \|<br>       CH$_3$ | navy blue | |
| 103 | | | " | navy blue | |
| 104 | | | " | reddish-tinged navy blue | |

-continued

| No. | Copper complex compound | Trihalogenotriazine | Component of the formula (V) | Colour shade | $\lambda_{max}$ (nm) |
|---|---|---|---|---|---|
| 105 | | triazine with F,F,F | " | navy blue | |
| 106 | | triazine with F,F,F | $HN-(CH_2)_2-SO_2-CH_2-CH_2OSO_3H$ with $CH_3$ on N | navy blue | |
| 107 | | triazine with F,F,F | " | dark blue | |

-continued

| No. | Copper complex compound | Trihalogenotriazine | Component of the formula (V) | Colour shade | $\lambda_{max}$ (nm) |
|---|---|---|---|---|---|
| 108 | | F,F,F-triazine | " | green | |
| 109 | | F,F,F-triazine | " | red-violet | |
| 110 | | Cl,Cl,Cl-triazine | $HN-(CH_2)_2-SO_2-CH_2-CH_2OSO_3H$, $CH_3$ | navy blue | 574 |

-continued

| No. | Copper complex compound | Trihalogenotriazine | Component of the formula (V) | Colour shade | $\lambda_{max}$ (nm) |
|---|---|---|---|---|---|
| 111 | | | " | navy blue | 568 |
| 112 | | | " | blue-violet | |

Other interesting dyestuffs, for example, from the ortho-disazo metal complex series are:

EXAMPLE 113

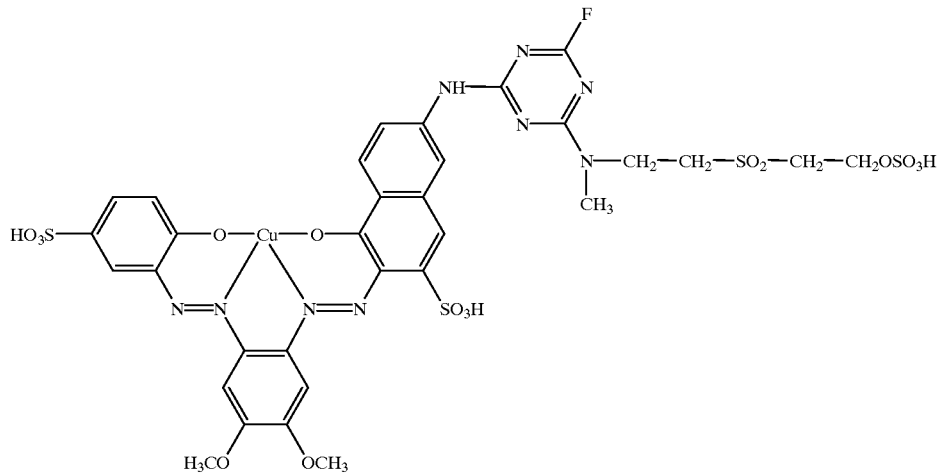

which dyes cotton in olive colour shades, or, from the ortho-aminoazo metal complex series, for example, the dyestuff of the formula $\lambda_{max}$=468 nm, 590 nm

EXAMPLE 114

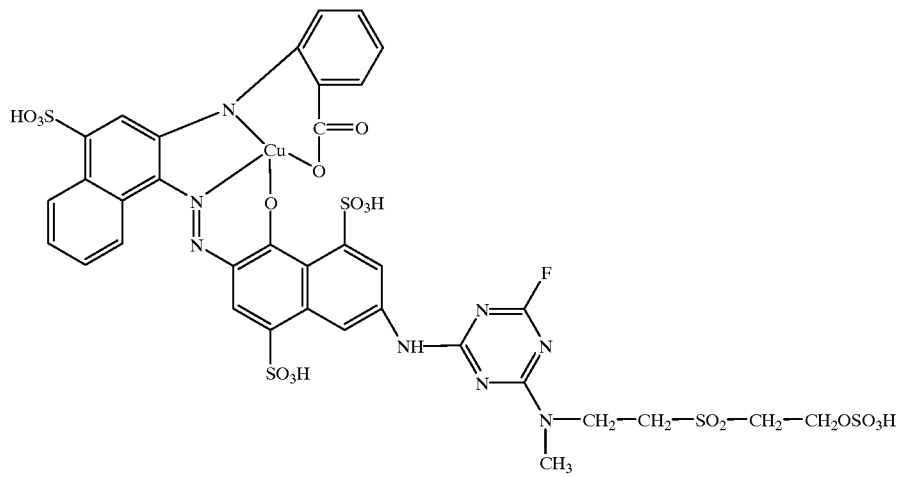

which dyes cotton in green shades.

EXAMPLE 115

0.1 mol of 1-amino-8-hydroxy-3,6-naphthalenedisulphonic acid was reacted with 2,4,6-trifluoro-1,3,5-triazine as Example 2 A) and with the compound of the formula (Va) analogously to Example 2 B).

0.1 mol of 1-sulpho-2-naphthylamine-6-β-sulphatoethylsulphone was diazotized in the customary manner and coupled to the E acid condensation product at pH 7.5–8.5. The dyestuff was salted out by addition of potassium chloride and isolated. Drying gave about 35 g of the salt-containing dyestuff of the formula

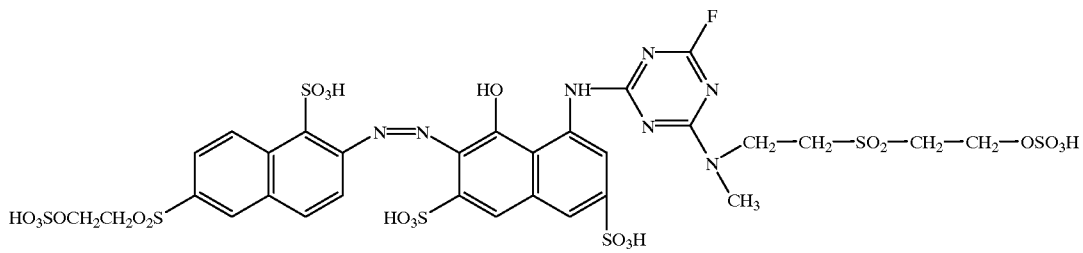

which dyes cotton in red colour shades by the dyeing or printing processes customary for reactive dyestuffs. $\lambda_{max}$= 519 nm, 541 nm Other red reactive dyestuffs were obtained by condensation of the following components:

EXAMPLE 116

0.1 mol of 4-(β-sulphatoethylsulphonyl)aniline was suspended in 200 parts of water and 100 parts of ice at 0° C. 28 parts of concentrated hydrochloric acid were added. A solution of 7 parts of sodium nitrite in 70 parts of water was added dropwise in the course of 15 minutes. After the mixture had been subsequently stirred for 30 minutes, the diazotization had ended. A pale yellow suspension resulted. The excess nitrite was destroyed with amidosulphonic acid.

This suspension was now metered into 0.1 mol of the H acid condensation product from Example 115 over a period of 15–20 minutes. Coupling was carried out at 20° C. and a pH of 7–8. The dyestuff was precipitated by addition of ethanol and isolated. Drying gave about 40 g of a dyestuff powder which has the structure

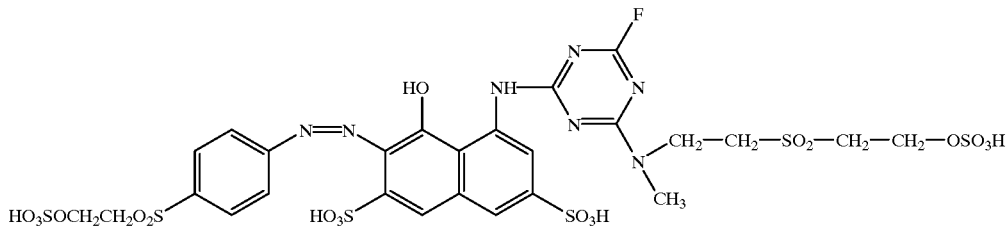

and which dyes cotton in red colour shades by the dyeing and printing processes customary for reactive dyestuffs. $\lambda_{max}$=515 nm Other red reactive dyestuffs were obtained by condensation of the following components:

| No. | Diazo component | 1-Amino-8-hydroxy-naphthalene-disulphonic acid | Trihalogenotriazine | Component of the formula (V) | Colour shade | $\lambda_{max}$ (nm) |
|---|---|---|---|---|---|---|
| 117 | 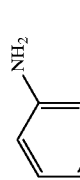 | 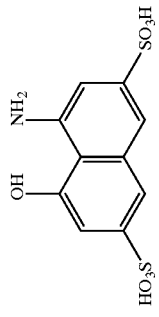 | 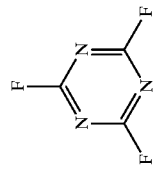 | HN—CH$_2$—CH$_2$—SO$_2$—CH$_2$—CH$_2$—OSO$_3$H \| CH$_3$ | red | |
| 118 | 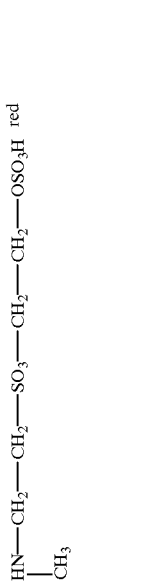 | 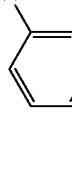 | 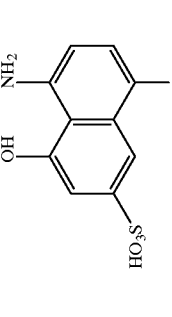 | " | red | |
| 119 | 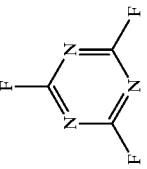 |  | 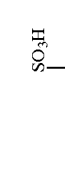 | " | red | 519, 534 |
| 120 | 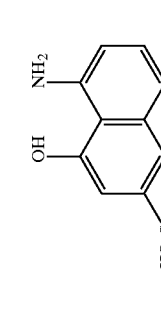 | 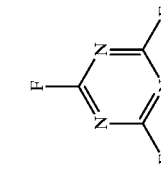 | 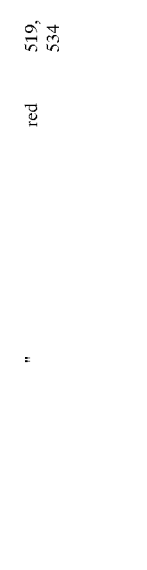 | " | red | 512, 534 |
| 121 | 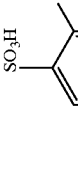 | 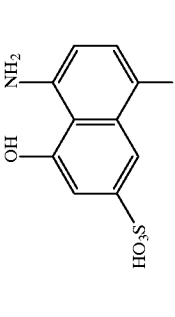 | 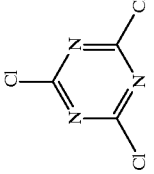 | HN—CH$_2$—CH$_2$—SO$_2$—CH$_3$—CH$_3$—OSO$_3$H \| CH$_3$ | red | |

-continued

| No. | Diazo component | 1-Amino-8-hydroxy-naphthalene-disulphonic acid | Trihalogenotriazine | Component of the formula (V) | Colour shade | $\lambda_{max}$ (nm) |
|---|---|---|---|---|---|---|
| 122 | 4-NH₂-C₆H₄-CH₂SO₂CH₂CH₂OSO₃H | 1-amino-8-hydroxy-3,6-disulpho naphthalene | 2,4,6-trichloro-triazine | " | red | |
| 123 | 2-amino-1-SO₃H-6-(SO₂CH₂CH₂OSO₃H)-naphthalene | 1-amino-8-hydroxy-3,6-disulpho naphthalene | 2,4,6-trichloro-triazine | " | red | 518, 540 |
| 124 | 3-NH₂-C₆H₄-SO₂CH₂CH₂OSO₃H | 1-amino-5-hydroxy-2,7-disulpho naphthalene | 2,4,6-trichloro-triazine | " | red | |
| 125 | 4-NH₂-C₆H₄-SO₂-CH₂-CH₃-OSO₃H | 1-amino-8-hydroxy-3,6-disulpho naphthalene | 2,4,6-trichloro-triazine | HN—CH₂—CH₂—SO₂—CH₂—CH₂—OSO₃H, CH₃ | red | 517 |
| 126 | 3-NH₂-C₆H₄-CH₂SO₂CH₂CH₂OSO₃H | 1-amino-8-hydroxy-3,6-disulpho naphthalene | 2,4,6-trifluoro-triazine | " | red | |

| No. | Diazo component | 1-Amino-8-hydroxy-naphthalene-disulphonic acid | Trihalogenotriazine | Component of the formula (V) | Colour shade | $\lambda_{max}$ (nm) |
|---|---|---|---|---|---|---|
| 127 | 3-NH₂-C₆H₄-SO₂CH₂CH₂OSO₃H | 1-NH₂-8-OH-naphthalene-3,6-(SO₃H)₂ | 2,4,6-trifluoro-1,3,5-triazine | " | red | 513 |
| 128 | 4-NH₂-C₆H₄-SO₂CH₂CH₂OSO₃H | 1-(4-NH₂-C₆H₄-CONH)-8-OH-naphthalene-3,6-(SO₃H)₂ | 2,4,6-trifluoro-1,3,5-triazine | " | red | |
| 129 | 4-NH₂-C₆H₄-SO₂CH₂CH₂OSO₃H | 1-(4-NH₂-C₆H₄-CONH)-8-OH-naphthalene-3,6-(SO₃H)₂ | 2,4,6-trichloro-1,3,5-triazine | " | red | |

EXAMPLE 130

0.1 mol of the monoazo compound having the formula

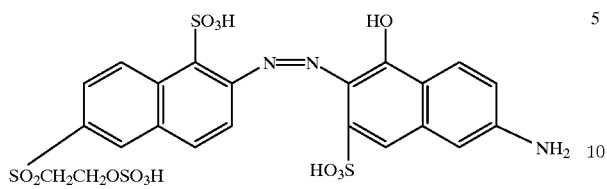

was reacted with 2,4,6-trifluoro-1,3,5-triazine and the compound of the formula Va analogously to Example 19.

The dyestuff was salted out by addition of potassium chloride, isolated and dried. About 82 g of a salt-containing dyestuff of the formula which has the structure

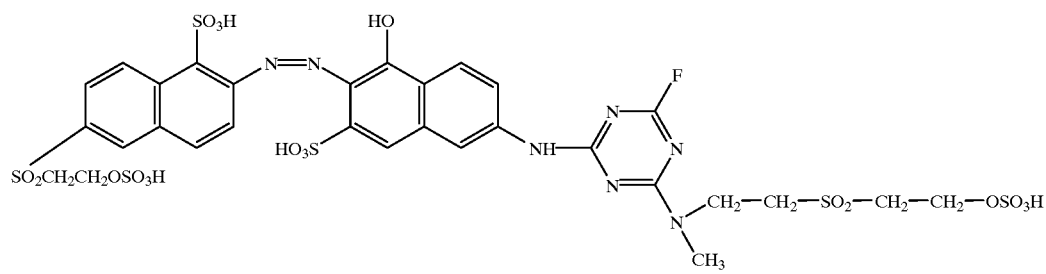

which dyes cotton in orange colour shades by the dyeing or printing processes customary for reactive dyestuffs were obtained. $\lambda_{max}$=492 nm

EXAMPLE 131

0.1 mol of (4-aminophenyl-β-sulphatoethyl)sulphone was diazotized as described in Example 116 and coupled with the I acid condensation product described in Example 2 A) and B).

The dyestuff of the formula

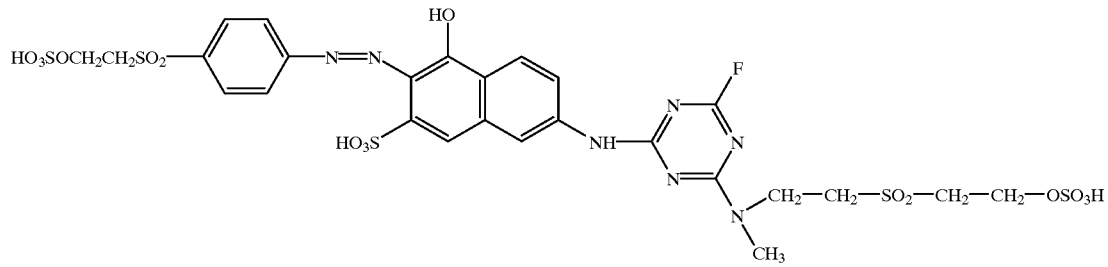

was salted out by addition of NaCl and isolated. Drying gave about 105 g of a dyestuff powder which dyes cotton in scarlet shades by the dyeing or printing processes customary for reactive dyestuffs. $\lambda_{max}$=479 nm Other reactive dyestuffs were obtained by condensation of the following components analogously to Example 130 or 131.

| No. | Aminoazo dyestuff | Component of the formula (V) | Halogenotriazine | colour shade | $\lambda_{max}$ (nm) |
|---|---|---|---|---|---|
| 132 | (naphthalene-azo-naphthalene structure with SO₃H, OH, NH₂, SO₂CH₂CH₂OSO₃H groups) | HNCH₂CH₂—SO₂—CH₂—CH₂OSO₃H with CH₃ branch | 2,4,6-trichlorotriazine | orange | 491 |
| 133 | (phenyl-azo-naphthalene structure with SO₂CH₂CH₂OSO₃H, OH, NH₂, HO₃S groups) | " | 2,4,6-trifluorotriazine | orange | 478 |
| 134 | (phenyl-azo-naphthalene structure with HO₃SOCH₂CH₂O₂SCH₂, OH, NH₂, HO₃S groups) | " | " | orange | |
| 135 | (phenyl-azo-naphthalene structure with HO₃SOCH₂CH₂O₂SCH₂, OH, NH₂, HO₃S groups) | " | " | orange | |

-continued

| No. | Aminoazo dyestuff | Component of the formula (V) | Halogenotriazine | colour shade | $\lambda_{max}$ (nm) |
|---|---|---|---|---|---|
| 136 | (structure with SO₃H, OH, NH₂, HO₃SOCH₂CH₂O₂S naphthalene azo) | HNCH₂CH₂—SO₂CH₂CH₂OS<br>\|<br>CH₃ | (trifluoropyrimidine with O₃H) | yellowish-tinged red | |
| 137 | (structure with SO₃H, OH, NH₂, HO₂SOCH₂CH₂SO₃ naphthalene azo) | " | (trichloropyrimidine) | yellowish-tinged red | |
| 138 | (structure with OH, NH₂, HO₂S, HO₃S—OH₂C—CH₂—O₂S naphthalene azo) | " | " | orange | 478 |

EXAMPLE 139

0.1 mol of the known compound

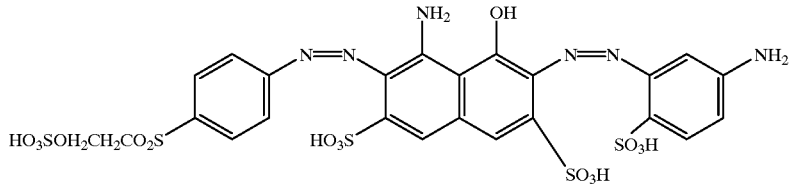

was reacted with 2,4,6-trifluoro-1,3,5-triazine and the compound of the formula (Va) analogously to Example 19.

When the condensation had ended, the dyestuff was isolated, after buffering to pH 6, either directly by spray drying or by salting out, filtration with suction and vacuum drying at 40° C. The dyestuff has the formula

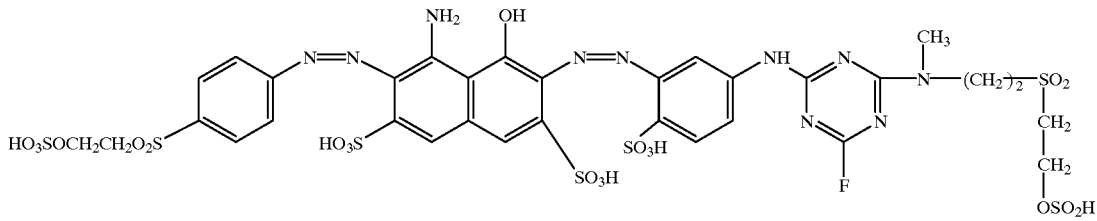

and dyes cotton in navy blue shades with very good yields by the dyeing techniques customary for reactive dyestuffs. $\lambda_{max}=612$ nm Other similar reactive dyestuffs which dye cellulose fibres navy blue to black were obtained when the aminodisazo components of the general formula

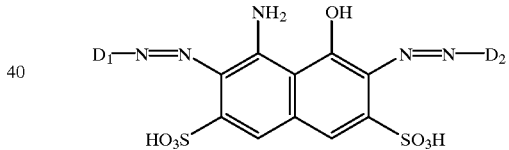

shown in the following list were subjected to condensation with the trihalogenotriazines and compounds of the formula (V).

| No. | Aminodisazo component | Trihalogenotriazine | Component of formula (V) | Colour shade | $\lambda_{max}$ (nm) |
|---|---|---|---|---|---|
| 140 | $D_1$ / 3-methylphenyl-SO$_2$CH$_2$CH$_2$OSO$_3$H ; SO$_3$H, CH$_3$, NH$_2$ aniline | 2,4,6-trifluorotriazine | HN—CH$_2$—CH$_2$—SO$_2$—CH$_2$—CH$_2$—OSO$_3$H, CH$_3$ | navy | |
| 141 | HO$_3$SOCH$_2$CH$_2$SO$_2$-(4-methylphenyl) ; SO$_3$H, CH$_3$, NH$_2$ aniline | 2,4,6-trichlorotriazine | " | navy | 613 |
| 142 | 3-methylphenyl-CH$_2$SO$_2$CH$_2$CH$_2$OSO$_3$H ; SO$_3$H, CH$_3$, NH$_2$ aniline | 2,4,6-trifluorotriazine | " | navy | |
| 143 | HO$_2$SOCH$_2$CH$_2$SO$_3$-(4-methylphenyl) ; SO$_3$H, CH$_3$, NH$_2$ aniline | 2,4,6-trifluorotriazine | " | navy | |

-continued

| No. | Aminodisazo component | Trihalogenotriazine | Component of formula (V) | Colour shade | $\lambda_{max}$ (nm) |
|---|---|---|---|---|---|
| 144 | HO₃SOCH₂CH₂SO₂CH₂–(p-C₆H₄)–  D₂–(phenyl with NH₂, SO₃H, SO₃H, CH₃) | 2,4,6-trifluorotriazine | HNCH₂CH₂–SO₂–CH₂–CH₂OSO₃H  \| CH₃ | black | |
| 145 | (m-C₆H₄) with SO₂CH₂CH₂OSO₃H and CH₃; aminophenyl with NH₂, SO₃H, CH₃ | 2,4,6-trichlorotriazine | " | navy | |
| 146 | naphthyl with SO₃H, CH₃, SO₂CH₂CH₂OSO₃H; aminophenyl with NH₂, SO₃H, CH₃ | 2,4,6-trifluorotriazine | " | black | |

EXAMPLE 147

A) 0.1 mol of 1-amino-8-hydroxynaphthalene-3,6-disulphonic acid was dissolved in 250 ml of water at pH 6.5 and the solution was cooled to 0° C. with 250 g of ice. 0.1 mol of 2,4,6-trifluoro-1,3,5-triazine (cyanuric fluoride) was added and the pH was kept between 3.5 and 4 with sodium carbonate solution. After 5 minutes, 0.1 mol of morpholine was added and the pH was brought to 7 with sodium carbonate solution. The temperature thereby rose to about 10° C.

B) 0.1 mol of 2,4-diaminobenzenesulphonic acid was stirred in 100 ml of water and 100 g of ice and dissolved under neutral conditions. 0.1 mol of 2,4,6-trichloro-1,3,5-triazine was added and initial condensation was carried out at pH 4–5; the pH was maintained with sodium carbonate solution. When the first condensation had ended, 0.1 mol of the compound of the formula (Va) was added. The second condensation was carried out at 30° C. and pH 8. A product of the formula

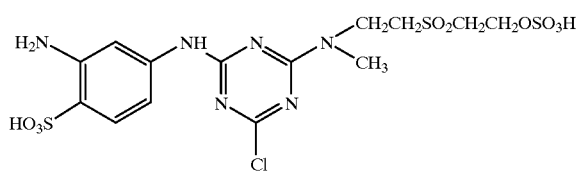

was obtained.

This diazo component was diazotized at 0° C. and pH 3–3.5 and added to the solution of the coupling component described above, a pH of 6–7 being established and maintained with sodium carbonate solution.

When the coupling had ended, the product was salted out with NaCl, isolated and dried. 81 g of salt-containing dyestuff of the formula

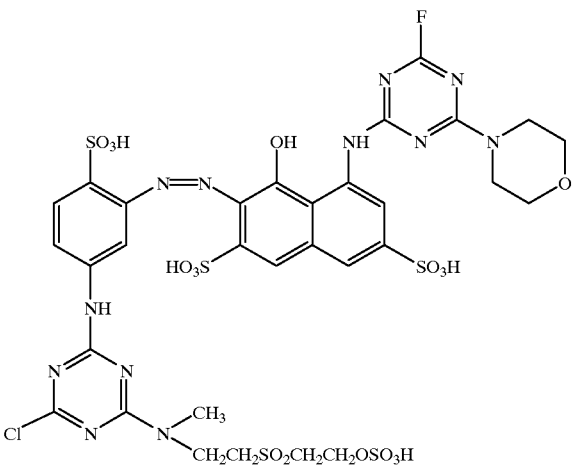

were obtained as a powder which dyes cotton in clear red shades. $\lambda_{max}$=514 nm, 533 nm The dyestuffs of the following examples were prepared analogously:

| Example | B | Diazo component | Coupling component | Y |
|---|---|---|---|---|
| 148 | 4-chloro-6-methylpyrimidin-2-yl with N(CH₃)CH₂CH₂CH₂—SO₂CH₂CH₂OSO₃H | 2-aminobenzene-1-sulfonic acid with NH—B at position 4 | 4-amino-5-hydroxy-6-methyl-naphthalene-1,7-disulfonic acid with NH—Y | 2-fluoro-6-methyl-4-morpholinopyrimidine |
| 149 | 4-chloro-6-methylpyrimidin-2-yl with N(CH₃)CH₂CH₂SO₂CH₂CH₂·OSO₃H | " | 6-amino-1-hydroxy-2-methylnaphthalene-3-sulfonic acid with NH—Y | 4-chloro-6-methyl-pyrimidin-2-yl-amino, 3-SO₃H-phenyl |
| 150 | 4-fluoro-6-methylpyrimidin-2-yl with N(CH₃)CH₂CH₂SO₂CH₂CH₂OSO₃H | 4-amino-benzene-1,3-disulfonic acid (with B—NH) | 7-amino-1-hydroxy-2-methylnaphthalene-3-sulfonic acid with NH—Y | 2-chloro-6-methyl-4-morpholinopyrimidine |
| 151 | 4-chloro-6-methylpyrimidin-2-yl with N(CH₃)CH₂CH₂—SO₂—CH₂O—SO₃H | 4-amino-benzene-1,3-disulfonic acid (with B—NH) | 4-amino-5-hydroxy-6-methyl-naphthalene-2,7-disulfonic acid with NH—Y | 2-fluoro-6-methyl-4-morpholinopyrimidine |

-continued
| Example | B | Diazo component | Coupling component | Y |
|---|---|---|---|---|
| 152 | 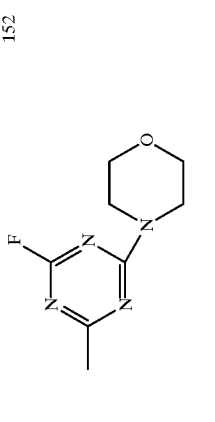 |  | 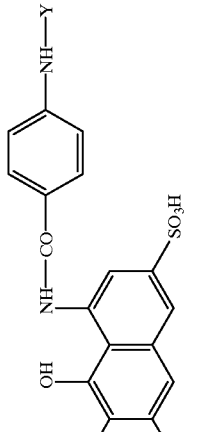 |  |
| 153 | | 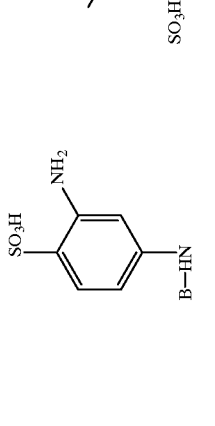 |  | " |
| 154 | 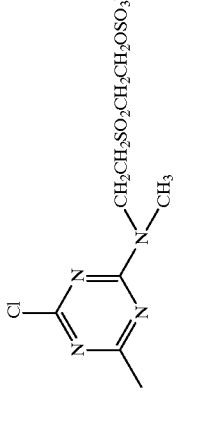 |  | 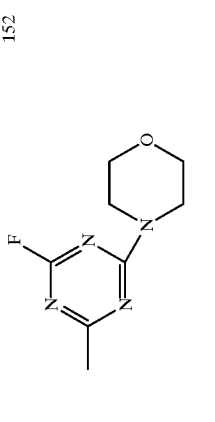 |  |
| 155 | 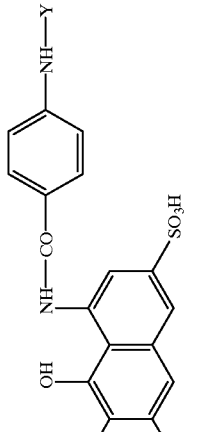 |  | | " |

-continued

| Example | B | Diazo component | Coupling component | Y |
|---|---|---|---|---|
| 156 | " | " | (structure) | (structure) |
| 157 | | (structure) | (structure) | (structure) |
| 158 | | (structure) | (structure) | (structure) |
| 159 | | (structure) | (structure) | (structure) |

EXAMPLE 160

0.2 mol of 1-amino-8-hydroxynaphthalene-3,6-disulphonic acid was dissolved in 450 ml of water with sodium hydroxide solution at pH 8–9, and 0.22 mol of 2,4,6-trifluoropyrimidine was added. The condensation was carried out at 35–40° C., the pH being maintained with sodium carbonate solution.

0.2 mol of the diazo component described in Example 147 B) was diazotized and coupled with the coupling component described above. Salting out, isolation and drying gave the dyestuff of the formula

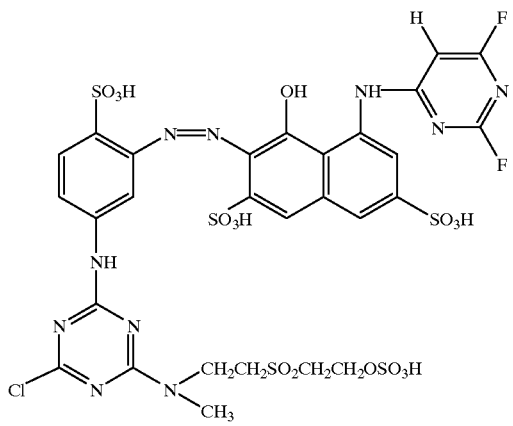

which dyes cotton in red shades.

EXAMPLE 161

0.2 mol of 8-(4'-amino-benzoylamino)-1-naphthol-3,6-disulphonic acid was dissolved in 800 ml of water with sodium carbonate solution (20 g/100 ml) at a pH of 7. The pH was brought to 4.5 with 10% strength HCl solution. 0.2 mol of 2,4,6-trifluoropyrimidine was added and the mixture was heated up to 30° C. A pH of 4.5–6 was maintained with sodium carbonate solution. The reaction had ended after 4 hours.

0.2 mol of the diazonium salt from Example 147 was now added, and at the same time a pH of 7.5–8 was maintained by dropwise addition of sodium carbonate solution. When the coupling had ended, the product was salted out with NaCl, isolated and dried. The dyestuff of the formula

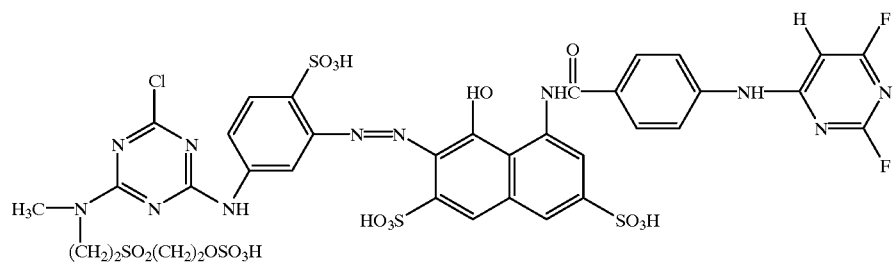

dyes cotton in red shades. $\lambda_{max}$=520 nm, 537 nm

The dyestuffs of Examples 163–174 were prepared analogously to Examples 160 and 161:

| B | Diazo component | Coupling component | Y | Example | $\lambda_{max}$ (nm) |
|---|---|---|---|---|---|
| Cl-pyrimidine-N(CH₃)-CH₂CH₂SO₂CH₂CH₂OSO₃H | 2-amino-4-(B-NH)-5-methyl-benzene with SO₃H | H-acid type (NH-Y, OH, SO₃H, HO₃S, CH₃) | 5-F, 4-Cl, 6-methyl pyrimidine | 163 | |
| " | 2-amino-4-(B-NH)-benzene-SO₃H | H-acid type | 5-F, 4-Cl, 6-methyl pyrimidine | 164 | |
| | 2-amino-4-[B-N(CH₃)]-benzene-SO₃H | " | | 165 | |
| Cl-pyrimidine-N(CH₃)-CH₂CH₂SO₂CH₂CH₂OSO₃H | 2-amino-4-(B-NH)-1,5-disulfo-benzene | K-acid type (NH-Y, OH, SO₃H, SO₃H, CH₃) | 2,6-difluoro-4-methyl pyrimidine | 166 | |

-continued
| B | Diazo component | Coupling component | Y | Example | $\lambda_{max}$ (nm) |
|---|---|---|---|---|---|
| 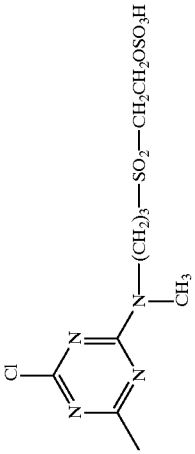 | 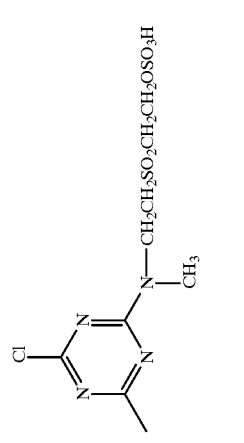 | 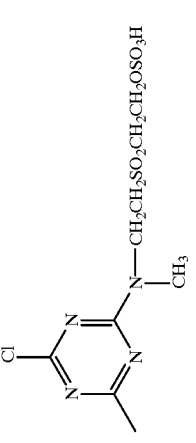 | 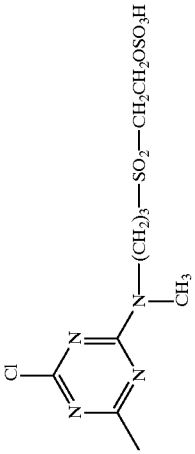 | 167 | 522 |
| 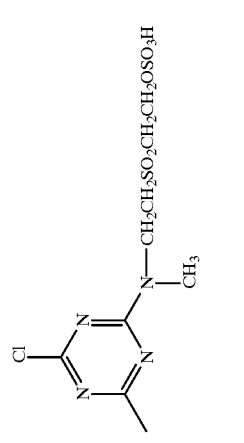 | 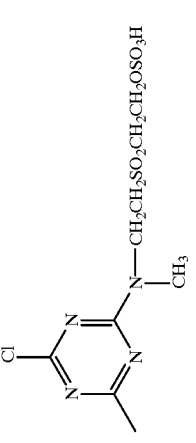 | 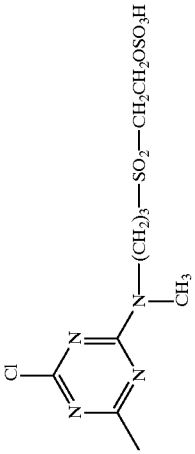 | 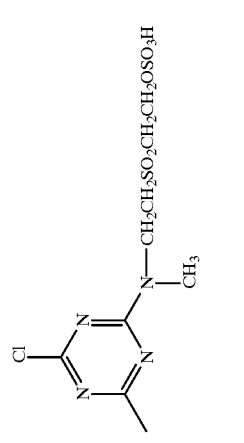 | 168 | |
| 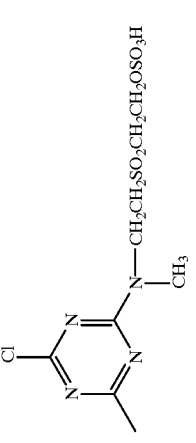 | 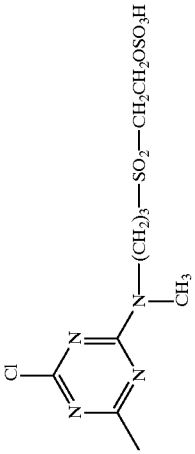 | 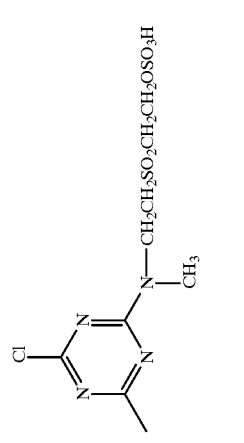 | 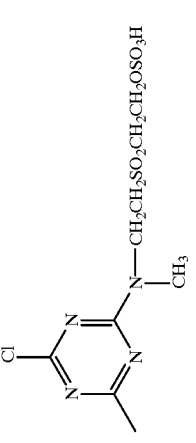 | 169 | |
| 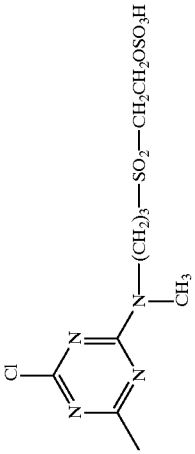 | 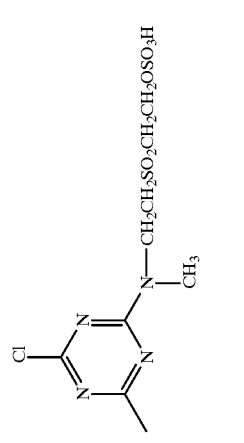 | 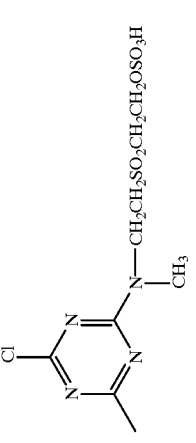 | 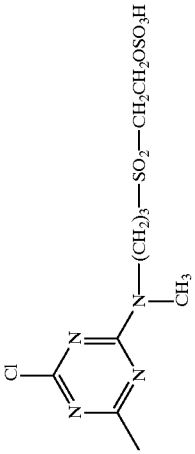 | 170 | |

-continued
| B | Diazo component | Coupling component | Example | Y | $\lambda_{max}$ (nm) |
|---|---|---|---|---|---|
|  | 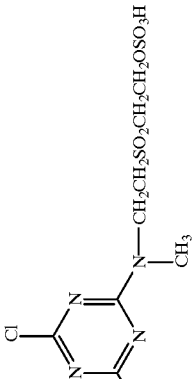 | " | 171 | 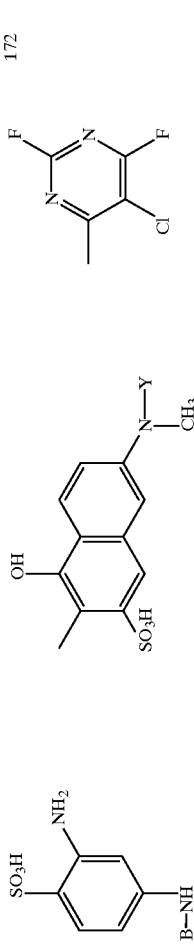 | |
| 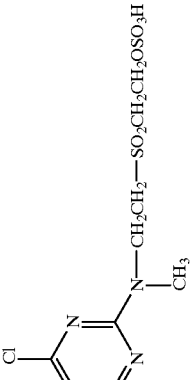 | 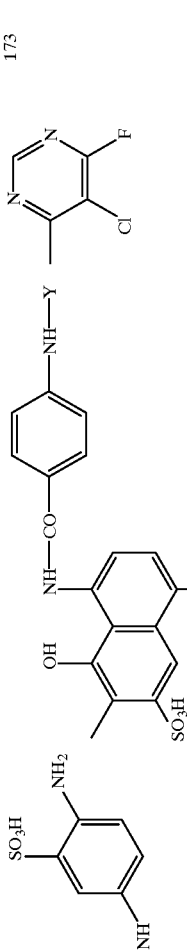 | 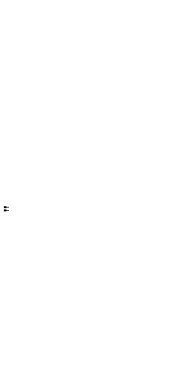 | 172 |  | |
| " | 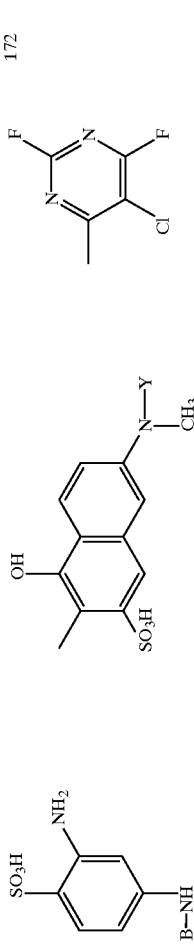 | 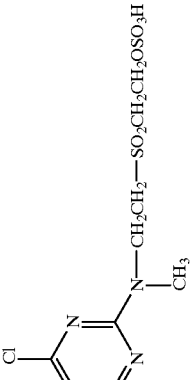 | 173 | 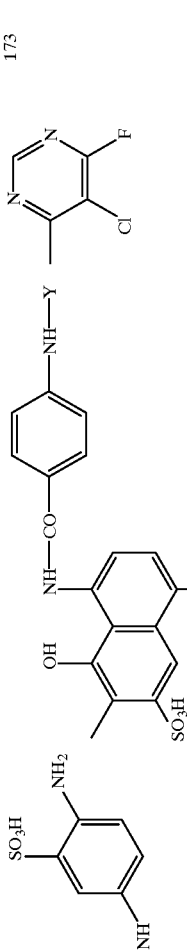 | |
| " | 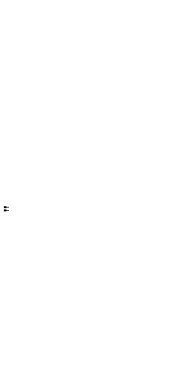 |  | 174 | 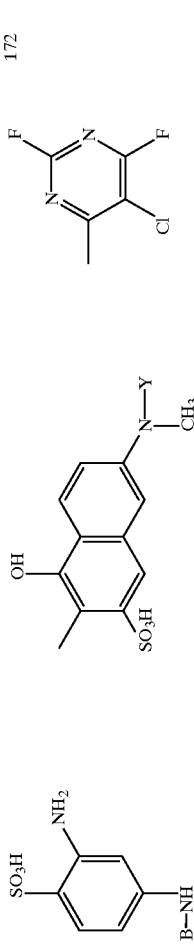 | |

EXAMPLE 175

0.22 mol of N-ethylaniline was dissolved in 200 ml of water with hydrochloric acid at pH 5. 200 g of ice were added and 0.24 mol of cyanuric chloride was sprinkled in. A pH of 5–6 was obtained with sodium carbonate solution. After about 1 hour at 0° C., the condensation had ended. 0.2 mol of 2,4-diamino-benzenesulphonic acid was dissolved in 250 ml of water by addition of concentrated sodium hydroxide solution and the solution was added to the first stage of the condensation. A pH of 6–7 was maintained with sodium carbonate solution. The mixture was heated up to 25–30° C. When the condensation had ended, the mixture was cooled to 0° C. 56 ml of 30% strength hydrochloric acid were added. 47 ml of sodium nitrite solution (30 g/100 ml) were added dropwise and the mixture was stirred at 0° C. for 1 hour. Sodium nitrite was destroyed with amidosulphonic acid and the diazotization mixture thus obtained was added to the coupling component from Example 1. A pH of 7–8 was maintained with sodium carbonate solution (20 g/100 ml). T=10–15° C. When the coupling had ended, the product was salted out with NaCl, isolated and dried. The resulting dyestuff of the formula

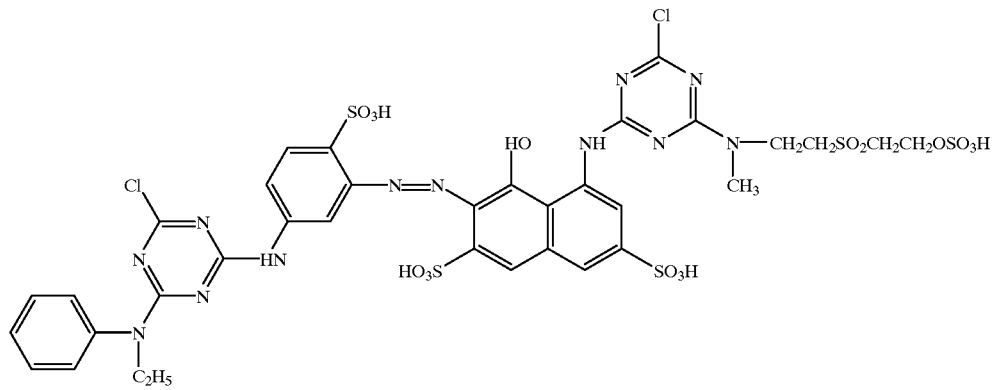

dyes cotton in red shades. $\lambda_{max}$ 515 nm, 533 nm

The dyestuff of Examples 176–178 were prepared analogously to Example 175:

| Example | Diazo component | Coupling component | Y | B |
|---|---|---|---|---|
| 176 | 5-amino-2-(Y-HN)-benzene-1,3-disulfonic acid type (SO₃H, NH₂, SO₃H, Y—HN) | 8-amino-1-hydroxy-2-methyl-naphthalene-4,6-disulfonic acid (NH—B, OH, SO₃H, CH₃, SO₃H) | 2-fluoro-4-methyl-6-(N-ethyl-N-phenyl-amino)-pyrimidine | 2-chloro-6-methyl-4-[N-(3-sulfatoethylsulfonyl-propyl)-N-methyl-amino]-pyrimidine |
| 177 | 2-amino-4-(Y-NH)-benzenesulfonic acid (NH₂, SO₃H, Y—NH) | 4-[(8-amino-1-hydroxy-3,6-disulfo-naphthalen-7-yl-carbonyl)-amino]-phenyl-NH—B | 2-chloro-6-methyl-4-(3-sulfophenyl-amino)-pyrimidine | " |
| 178 | 3-amino-4-(Y-N(CH₃)-CH₂)-benzenesulfonic acid (NH₂, SO₃H, Y—N, CH₃, CH₂) | " | 2-fluoro-6-methyl-4-[N-(2-hydroxyethyl)-N-phenyl-amino]-pyrimidine | " |

EXAMPLE 179

0.2 mol of 6-fluoro-5-chloro-4-(3'-amino-4'-sulphophenyl)-amino-pyrimidine (prepared from 2,4-diaminobenzenesulphonic acid and 4,6-difluoro-5-chloropyrimidine) was suspended in water, and 65 ml of 30% strength hydrochloric acid and 300 g of ice were added. Thereafter, 46 ml of 30% strength sodium nitrite solution were added and the mixture was stirred at 0° C. for 1 hour. Excess sodium nitrite was destroyed with amidosulphonic acid and the diazotization mixture thus obtained was added to the solution of the coupling component from Example [lacuna]. A pH of 7–8 was maintained with sodium carbonate solution. T=10–15° C. When the coupling had ended, the product was salted out with NaCl, isolated and dried. The resulting dyestuff of the formula

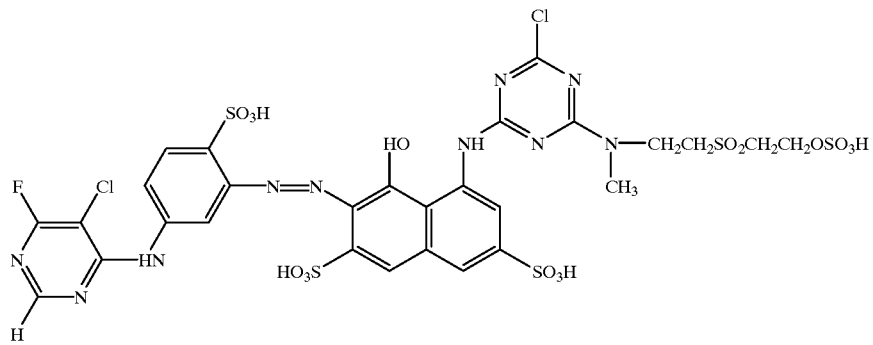

dyes cotton in red shades.

The dyestuffs of Examples 180–182 were prepared analogously to Example 179:

| Example | Diazo component | Coupling component | Y | B |
|---|---|---|---|---|
| 180 | ![](SO3H, NH2, Y—HN, SO3H) | ![](OH, NH—B, CH3, SO3H, SO3H) | ![](CH3, F, N, N, F) | ![](Cl, N, N, N, CH3, N—CH2CH2SO3CH2CH2OSO2H, CH3) |
| 181 | ![](SO3H, NH2, Y—NH) | ![](OH, NH—B, CH3, SO3H, SO3H) | " | ![](CH3, N, N, N, CH3, N—CH2CH2SO3CH2CH2OSO2H, F) |
| 182 | ![](SO3H, NH2, Y—N—CH2, CH3) | ![](OH, CH3, SO3H, NH—B) | ![](Cl, N, F, N, CH3, F) | " |

EXAMPLE 183

0.1 mol of the copper complex of N-(2-carboxy-5-sulphophenyl)-N'-(2'-hydroxy-3'-amino-5'-sulphophenyl)-ms-phenyl-formazan disodium salt was dissolved in 600 ml of water. After cooling to 0° C., 0.12 mol of 2,4,6-trifluoro-1,3,5-triazine was added dropwise and the pH was kept at 7.0 by addition of sodium carbonate solution. After addition of 0.11 mol of the compound of the formula (Va), the pH was kept at 8 with sodium carbonate solution and the tempera ture was allowed to rise gradually to 20° C. When the condensation had ended, the dyestuff was salted out, isolated and, after buffering at pH 6, dried at 45° C. in vacuo.

The dyestuff corresponds to the formula

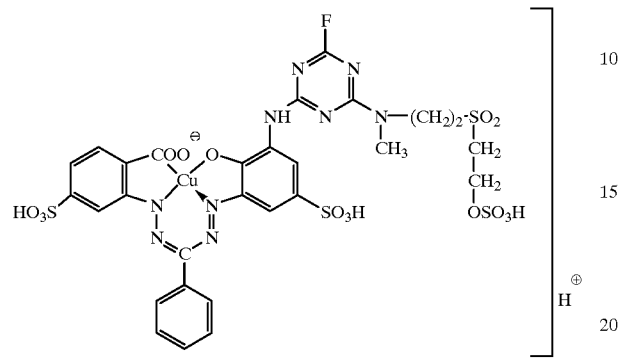

and dyes cotton in blue shades with very good fixing yields from a long liquor. $\lambda_{max}$=609 nm Other blue formazan dyestuffs were obtained by condensation of the following components:

| No. | Aminoformazan | Trihalogenotriazine | Component of the formula (V) | Colour shade | $\lambda_{max}$ (nm) |
|---|---|---|---|---|---|
| 184 | N-(2-Carboxy-5-sulphophenyl)-N'-(2'-hydroxy-5'-amino-3'-sulphophenyl)-ms-2"-sulphophenyl)-formazan, Cu complex | ![F,F,F triazine] | HN—(CH$_2$)$_2$—SO$_2$—CH$_2$—CH$_2$—OSO$_3$H<br>  \|<br>  CH$_3$ | blue | |
| 185 | N-(2-Hydroxy-3-amino-5-sulphophenyl)-N'-(2'-hydroxy-4'-sulphophenyl)-ms-(2"-sulphophenyl)-formazan, Cu complex | ![F,F,F triazine] | " | navy blue | |
| 186 | N-(2-Carboxy-5-sulphophenyl)-N'-2-hydroxy-5'-amino-3'-sulphophenyl)-ms-4"-sulphophenyl)-formazan, Cu complex | ![F,F,F triazine] | " | blue | |
| 187 | N-(2-Carboxy-4-sulphophenyl)-N'-(2'-hydroxy-3'-amino-5'-sulphophenyl)-ms-phenyl-formazan, Cu complex | ![F,F,F triazine] | " | blue | |
| 188 | N-(2-Carboxy-5-sulphophenyl)-N'-(2'-hydroxy-3'-amino-5'-sulphophenyl)-ms-phenyl-formazan, Cu complex | ![Cl,Cl,Cl triazine] | HN—(CH$_2$)$_2$—SO$_2$—CH$_2$—CH$_2$—OSO$_3$H<br>  \|<br>  CH$_3$ | blue | 610 |

-continued

| No. | Aminoformazan | Trihalogenotriazine | Component of the formula (V) | Colour shade | $\lambda_{max}$ (nm) |
|---|---|---|---|---|---|
| 189 | N-(2-Carboxy-4-sulphophenyl)-N'-(2'-hydroxy-3'-amino-5'-sulphophenyl)-ms-phenyl-formazan, Cu complex | 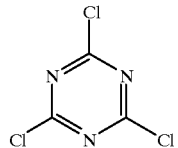 | " | blue | |
| 190 | N-(2-Hydroxy-3-amino-5-sulpho-phenyl)-N'-(2'-carboxy-4-sulphophenyl)-ms-(2"-chloro-5"-sulphophenyl)-formazan, Cu complex | 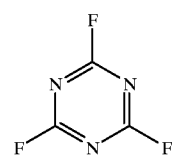 | NHCH$_2$—CH$_2$—SO$_2$—CH$_2$—CH$_2$—OSO$_2$H<br>\|<br>CH$_3$ | blue | |
| 191 | N-(2-Hydroxy-5-amino-3-sulpho-phenyl)-N'-(2',5'-disulpho-phenyl)-ms-phenyl-formazan, Cu complex | 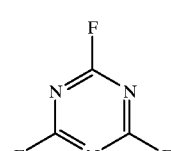 | " | blue | |
| 192 | N-(2-Carboxy-5-sulphophenyl)-N'-(2'-hydroxy-3'-amino-5'-sulphophenyl)-ms-(2"-sulphophenyl)-formazan, Cu complex | 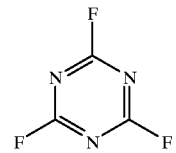 | NHCH$_2$—CH$_2$—SO$_2$—CH$_2$CH$_2$OSO$_3$H<br>\|<br>CH$_3$ | blue | |
| 193 | N-(2-Carboxy-5-sulphophenyl)-N'-(2'-hydroxy-3',5'-disulphophenyl)-ms-(3"-amino-phenyl)-formazan, Cu complex | 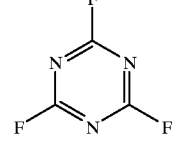 | " | greenish-tinged blue | |
| 194 | N-(2-Carboxy-5-sulphophenyl)-N'-(2'-hydroxy-3'-amino-5'-sulpho-phenyl)-ms-(2"-sulphophenyl)-formazan, Cu complex | 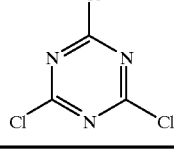 | " | blue | |

EXAMPLE 195

0.1 mol of the anthraquinone of the formula

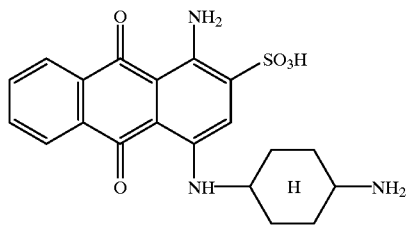

was dissolved in about 1000 parts of water with potassium hydroxide solution at a pH of 12 to 13. The dyestuff solution was clarified, and 200 parts of hexahydro-2H-azepin-2-one were added. Initial condensation was carried out with 0.11 mol of cyanuric chloride at 0° C. The second condensation was carried out at pH 8 and 30° C. after addition of 0.1 mol of the compound of the formula (Va).

The dyestuff was precipitated with ethanol, isolated and dried. About 200 g of a reactive dyestuff of the formula

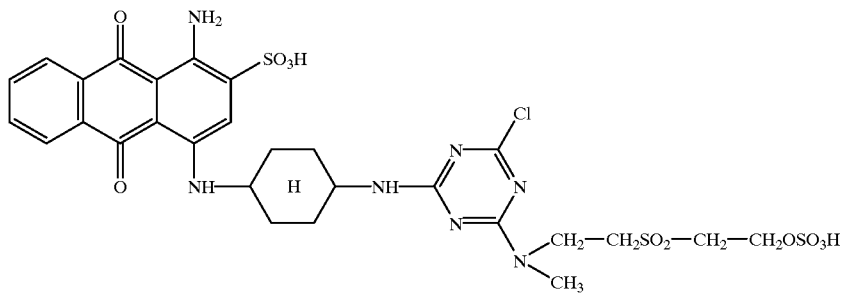

which dyes cotton in blue colour shades by the dyeing or printing processes customary for reactive dyestuffs were obtained. $\lambda_{max}$=593 nm, 640 nm Other blue anthraquinone dyestuffs having similar properties were obtained by subjecting the anthraquinone components of the general formula

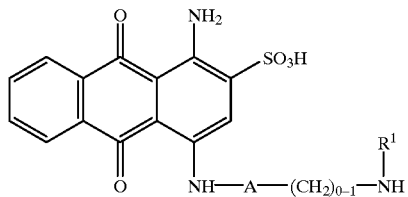

shown below to condensation with the trihalogenotriazines and the component of the formula (Va) by one of the methods described above.

| No. | —NH—A—(CH$_2$)$_{0-1}$—NR$^1$H | Trihalogenotriazine | Component of the formula (V) | Colour shade | $\lambda_{max}$ (nm) |
|---|---|---|---|---|---|
| 196 | ![benzene with NH, CH$_2$-NH-CH$_3$, SO$_3$H] | 2,4,6-trichloro-1,3,5-triazine | HN(CH$_3$)—(CH$_2$)$_2$—SO$_2$—CH$_2$—CH$_2$—OSO$_3$H | blue | 599 |
| 197 | ![benzene with NH$_2$, SO$_3$H] | 2,4,6-trifluoro-1,3,5-triazine | " | blue | 595 |
| 198 | ![trimethylbenzene with CH$_2$-NH$_2$, SO$_3$H] | 2,4,6-trichloro-1,3,5-triazine | " | reddish-tinged blue | |
| 199 | ![benzene with SO$_3$H, NH-CH$_3$] | 2,4,6-trifluoro-1,3,5-triazine | " | blue | 610 |

-continued

| No. | —NH—A—(CH$_2$)$_{0-1}$—NH(R$^1$) | Trihalogenotriazine | Component of the formula (V) | Colour shade | $\lambda_{max}$ (nm) |
|---|---|---|---|---|---|
| 200 | 2-amino-4-(NH—)-benzenesulfonic acid (SO$_3$H, NH$_2$, —NH—) | 2,4,6-trifluoro-1,3,5-triazine | HN(CH$_3$)—(CH$_2$)$_2$—SO$_2$—CH$_2$—CH$_2$—OSO$_3$H | greensih-tinged blue | 605 |
| 201 | —NH-, CH$_2$—NH$_2$, HO$_3$S, CH$_3$ substituted benzene | 2,4,6-trichloro-1,3,5-triazine | " | reddish-tinged blue | 584, 618 |
| 202 | —HN, CH$_3$, NH$_2$, SO$_3$H substituted benzene | 2,4,6-trifluoro-1,3,5-triazine | " | reddish-tinged blue | 591, 619 |
| 203 | —HN, CH$_3$, NH$_2$, SO$_3$H substituted benzene | 2,4,6-trichloro-1,3,5-triazine | " | reddish-tinged blue | 592, 618 |

EXAMPLE 204

32 g of copper phthalocyanine component of the formula

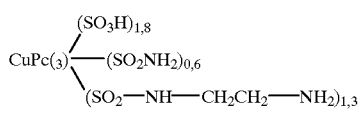

prepared in accordance with European Patent Specification 0 073 267, were dissolved in 300 ml of water at pH 7.0 to 7.5 and reacted with 2,4,6-trichloro-1,3,5-triazine and the compound of the formula (Va) analogously to Example 195.

When the reaction had ended, the resulting product was salted out of the solution, filtered off with suction, buffered with a little phosphate solution at pH 6.0 and dried in vacuo at 45° C. The dyestuff corresponds to the formula

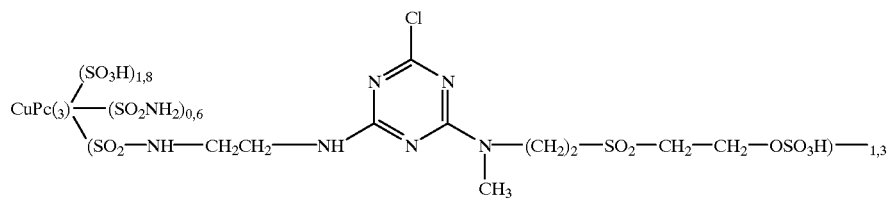

and dyes and prints cotton in fast turquoise blue shades with a good yield by the processes known for reactive dyestuffs. $\lambda_{max}$=663, 622 nm Other phthalocyanine reactive dyestuffs were obtained by subjecting the phthalocyanine components shown in the following list, trihalogenotriazines and the components of the formula (Va) to condensation with one another by the methods described in Examples 183 and 195.

| No. | Phthalocyanine component | Trihalogenotriazine | Component of the formula (V) | Colour shade | $\lambda_{max}$ (nm) |
|---|---|---|---|---|---|
| 205 | —NIP$_{c(3)}$ (SO$_3$H)$_{2.5}$ / (SO$_2$—NH—CH$_2$—CH$_2$—NH$_2$)$_{1.3}$ | 2,4,6-trichloro-1,3,5-triazine | HN—(CH$_2$)$_2$—SO$_2$—(CH$_2$)$_2$—OSO$_3$H / CH$_3$ | bluish-tinged green | 657, 623 |
| 206 | CuPc$_{(3)}$ (SO$_3$H)$_{2.9}$ / SO$_2$—NH—(phenyl with SO$_3$H, NH$_2$) | 2,4,6-trifluoro-1,3,5-triazine | " | turquoise | |
| 207 | CuPc$_{(3)}$ (SO$_3$H)$_{2.9}$ / SO$_2$—NH—(phenyl with NH$_2$) | 2,4,6-trichloro-1,3,5-triazine | " | turquoise | 667, 623 |
| 208 | CuPc$_{(3)}$ (SO$_3$H)$_{2.4}$ —(SO$_2$NH$_2$)$_{0.5}$ / SO$_2$—NH—(phenyl with NH$_2$, SO$_3$H) | 2,4,6-trifluoro-1,3,5-triazine | " | turquoise | |

EXAMPLE 209

22.1 g of triphendioxazine compound of the formula

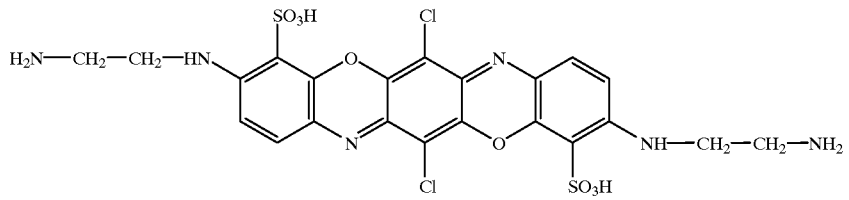

were dissolved in 300 ml of water by addition of sodium hydroxide solution at pH 11.5 to 12, and reacted with 2,4,6-trichloro-1,3,5-triazine and the compound of the formula (Va) analogously to Example 195.

The dyestuff was salted out, filtered off with suction and, after buffering at pH 6.7, dried at 45° C. in vacuo.

It corresponds to the formula

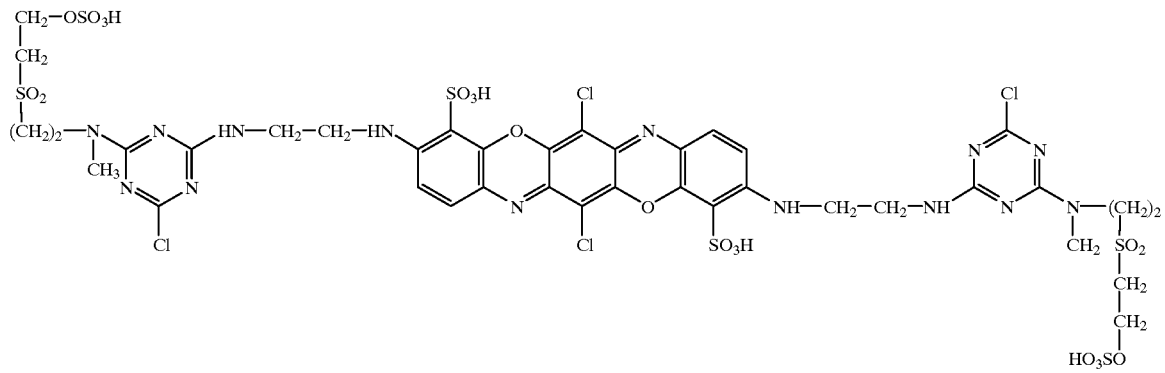

and dyes cotton in strong blue shades with good fixing yields by the customary methods. $\lambda_{max}$=622 nm

EXAMPLE 210

50 g of triphendioxazine compound of the formula

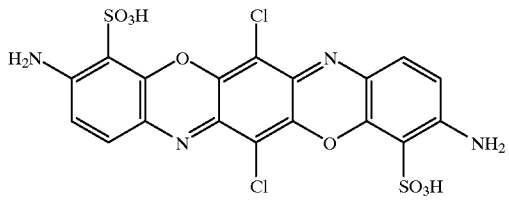

were dissolved in 2000 ml of water with 10% strength lithium hydroxide by establishing a pH of 7.0, and reacted with 2,4,6-trifluoro-1,3,5-triazine and the compound of the formula (Va) analogously to Example 183.

The condensation product was salted out, isolated and dried.

The resulting dyestuff corresponds to the formula

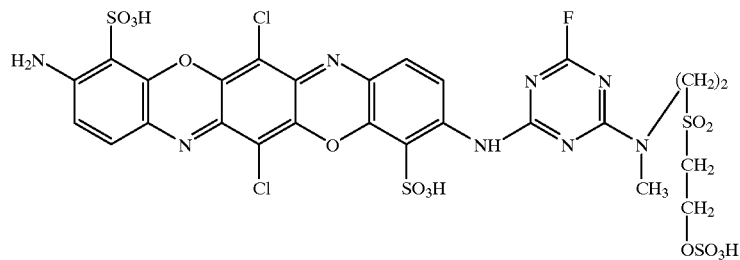

and dyes cotton in strongly reddish-tinged blue shades from a long liquor. $\lambda_{max}$=580 nm Other triphendioxazine reactive dyestuffs were prepared in an analogous procedure to Examples 183 and 195 by condensation of the following components:

| No. | Tripehnodioxazine | Trihalogenotriazine | Component of the formula (V) | Colour shade | $\lambda_{max}$(nm) |
|---|---|---|---|---|---|
| 211 | | | Product type corresponds to that from Example 209 | red | |
| 212 | | | Product type corresponds to that from Example 209 | blue | 624 |
| 213 | | | Product type corresponds to that from Example 210 | blue | 580 |

We claim:
1. Reactive dyestuff of the formula (I)

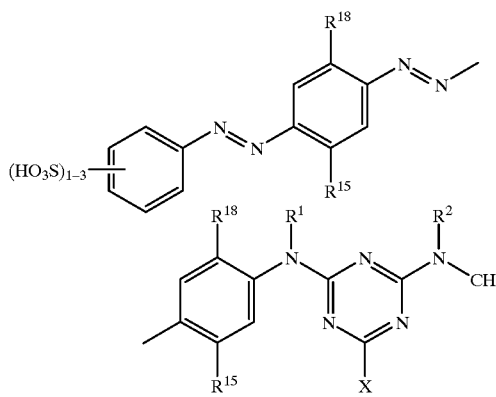

wherein
$R^1$ denotes H or unsubstituted or substituted $C_1$–$C_4$-alkyl,
$R^2$ denotes $C_1$–$C_4$-alkyl,
X denotes F, Cl or Br,
Z denotes —CH=CH$_2$ or —CH$_2$CH$_2$—OSO$_3$H,
$R^{15}$ denotes H, $C_1$–$C_4$-alkyl, $C_1$–$C_4$-alkoxy, Cl, Br, acylamino, amino carbonylamino, $C_1$–$C_4$-alkylsulphonylamino or arylsulphonylamino and
$R^{18}$ denotes H, $C_1$–$C_4$-alkyl, $C_1$–$C_4$-alkoxy, OH or SO$_3$H.

2. The reactive dyestuff according to claim 1, wherein the reactive dye of the formula (I) is a reactive dye of the formula (Ia)

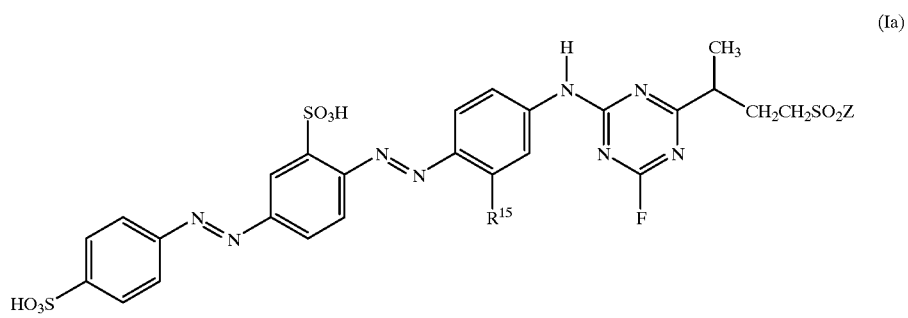

wherein
Z denotes —CH=CH$_2$ or —CH$_2$CH$_2$—OSO$_3$H and
$R^{15}$ denotes $C_1$–$C_4$-alkylcarbonylamino or amino carbonylamino.

3. A process for the preparation of a reactive dyestuff of the formula (I)

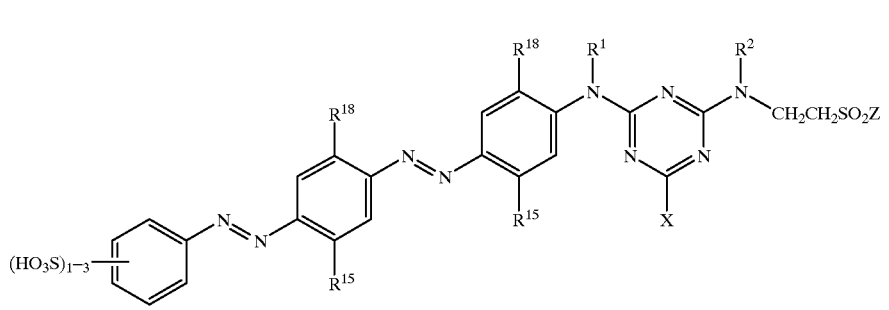

wherein
$R^1$ denotes H or unsubstituted or substituted $C_1$–$C_4$-alkyl,
$R^2$ denotes $C_1$–$C_4$-alkyl,
X denotes F, Cl or Br,
Z denotes —CH=CH$_2$ or —CH$_2$CH$_2$—OSO$_3$H,
$R^{15}$ denotes H, $C_1$–$C_4$-alkyl, $C_1$–$C_4$-alkoxy, Cl, Br, acylamino, amino carbonylamino, $C_1$–$C_4$-alkylsulphonylamino or arylsulphonylamino and
$R^{18}$ denotes H, $C_1$–$C_4$-alkyl, $C_1$–$C_4$-alkoxy, OH or SO$_3$H,
by which comprises a) condensation of a dyestuff of the formula (II)

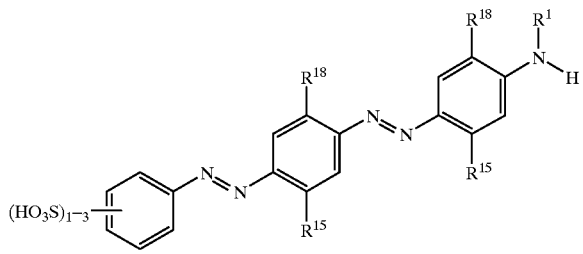
(II)

wherein $R^1$, $R^{15}$ and $R^{18}$ have the abovementioned meaning, with one mole of trifluorotriazine of the formula (III)

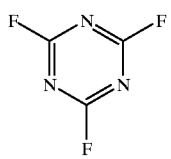
(III)

to give compounds of the formula (IV)

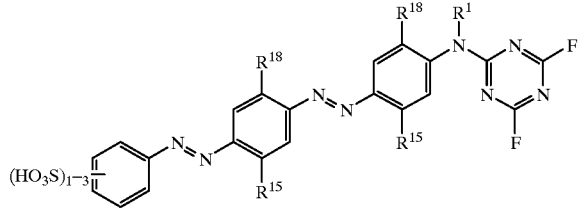
(IV)

and further condensation of the compounds of the formula (IV) with one mole of the compound of the formula (V)

$$R^2-NH-CH_2CH_2-SO_2-Z \quad (V)$$

wherein $R^2$ and Z have the above-mentioned meaning, or b) in the reverse sequence, by condensation of trifluorotriazine of the formula (III) with the compounds of the formula (V) to give the primary condensation product

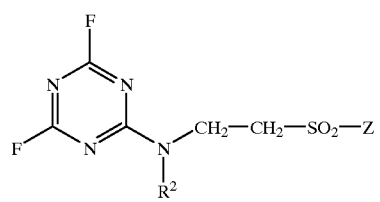
(VI)

wherein $R^2$ and Z have the abovementioned meaning, and further condensation of one mole of the compound of the formula (VI) with the dyestuff of the formula (III).

4. A textile product composing a material containing hydroxyl groups or amide groups which have been dyed with dyestuff according to claim 1.

5. A method for dyeing or printing a naturally occurring or a synthetic material containing hydroxy groups or amide groups which comprises contacting said naturally occurring or synthetic material with the reactive dyestuff according to claim 1.

* * * * *